(12) United States Patent
Bailey et al.

(10) Patent No.: US 12,194,171 B2
(45) Date of Patent: Jan. 14, 2025

(54) LIGHTING DEVICE WITH INTEGRAL UV DISINFECTION

(71) Applicant: HLI SOLUTIONS, INC., Greenville, SC (US)

(72) Inventors: Christopher Bailey, Greenville, SC (US); Douglas Hamilton, Arlington Heights, IL (US); Christopher Hutchins, Shelton, CT (US); Derek Baker, Middleboro, MA (US); Jason Duckworth, Simpsonville, SC (US); Dan Hassert, Shelton, CT (US); John Riley, Shelton, CT (US); Thomas Hill, Spartanburg, SC (US); Bruce Rhodes, Inverness, IL (US); Landon Gennetten, Shelton, CT (US); Thomas Benton, Shelton, CT (US); Jeffrey Schoepf, Marshfield, MA (US); Jeffrey McClow, Greer, SC (US)

(73) Assignee: HLI SOLUTIONS, INC., Greenville, SC (US)

( * ) Notice: Subject to any disclaimer, the term of this patent is extended or adjusted under 35 U.S.C. 154(b) by 853 days.

(21) Appl. No.: 17/342,250

(22) Filed: Jun. 8, 2021

(65) Prior Publication Data

US 2021/0379222 A1    Dec. 9, 2021

Related U.S. Application Data

(60) Provisional application No. 63/056,184, filed on Jul. 24, 2020, provisional application No. 63/051,430,
(Continued)

(51) Int. Cl.
*F21V 7/00*     (2006.01)
*A61L 2/10*     (2006.01)
(Continued)

(52) U.S. Cl.
CPC ........ *A61L 2/10* (2013.01); *A61L 2/24* (2013.01); *A61L 2/26* (2013.01); *F21V 7/005* (2013.01);
(Continued)

(58) Field of Classification Search
None
See application file for complete search history.

(56) References Cited

U.S. PATENT DOCUMENTS

| 2009/0049985 A1* | 2/2009 | Leroux | B01D 53/885 |
| | | | 95/79 |
| 2012/0199005 A1* | 8/2012 | Koji | F21V 17/06 |
| | | | 96/224 |

(Continued)

FOREIGN PATENT DOCUMENTS

JP     05-021951 U  *  3/1993

OTHER PUBLICATIONS

Document titled JP,05-021951,U(1993), English machine translation of JP 05-02195 U provided by J-PlatPat, original document published 1993 (Year: 1993).*

(Continued)

*Primary Examiner* — Holly Kipouros
(74) *Attorney, Agent, or Firm* — Buckley, Maschoff & Talwalkar LLC

(57) ABSTRACT

A luminaire includes a housing configured to be positioned over an area, the housing including a frame having a first channel for receiving a light emitter. A light emitter is positioned in the first channel. The light emitter is configured to emit ultra-violet light. A reflector assembly is connected to the frame to direct ultra-violet light emitted from the light emitter. At least a portion of the area is located at 0 degrees relative to the light emitter and a majority of the
(Continued)

emitted ultra-violet light is emitted from the housing between 90 degrees and 130 degrees relative to the light emitter in a first direction.

18 Claims, 21 Drawing Sheets

Related U.S. Application Data filed on Jul. 14, 2020, provisional application No. 63/036,216, filed on Jun. 8, 2020.

(51) Int. Cl.
  *A61L 2/24* (2006.01)
  *A61L 2/26* (2006.01)
  *F21V 17/00* (2006.01)
  *F21V 21/008* (2006.01)
  *F21V 21/02* (2006.01)
  *F21V 23/04* (2006.01)

(52) U.S. Cl.
  CPC .......... *F21V 17/002* (2013.01); *F21V 21/008* (2013.01); *F21V 21/02* (2013.01); *F21V 23/0435* (2013.01); *F21V 23/0478* (2013.01); *A61L 2202/11* (2013.01); *A61L 2202/14* (2013.01); *A61L 2202/25* (2013.01)

(56) References Cited

U.S. PATENT DOCUMENTS

| | | | |
|---|---|---|---|
| 2014/0084185 A1* | 3/2014 | Palmer | F21V 7/005 250/504 R |
| 2016/0175475 A1 | 6/2016 | DuPuis et al. | |
| 2017/0246329 A1 | 8/2017 | Lloyd | |
| 2017/0307182 A1 | 10/2017 | Seward et al. | |
| 2017/0312379 A1 | 11/2017 | Stibich | |
| 2018/0304226 A1 | 10/2018 | Khoshbin et al. | |
| 2019/0032875 A1 | 1/2019 | Ogg et al. | |
| 2019/0105415 A1* | 4/2019 | Gross | A61L 2/10 |
| 2019/0247528 A1* | 8/2019 | Rodriguez | A61L 2/26 |

OTHER PUBLICATIONS

PCT/US2021/036433 International Search Report and Written Opinion dated Sep. 16, 2021 (15 pages).

\* cited by examiner

LIGHTING DEVICE WITH INTEGRAL UV DISINFECTION

RELATED APPLICATIONS

This application claims benefit of U.S. Provisional Application Ser. No. 63/036,216 filed Jun. 8, 2020, U.S. Provisional Application Ser. No. 63/051,430 filed Jul. 14, 2020, and U.S. Provisional Application Ser. No. 63/056,184, filed Jul. 24, 202, the disclosures of which are incorporated herein by reference in their entirety and to which priority is claimed.

BACKGROUND

The application relates to luminaires and components for luminaires.

Light fixtures, or luminaires, include electric light sources and provide an aesthetic and functional housing in both interior and exterior applications. Wall pack luminaires may provide exterior lighting for buildings around walkways and exit doors, and may provide interior lighting near hallways, entryways, or other areas. Wall pack luminaires are typically secured to walls or other structures and provide downward light distribution from an elevated position. Pendant lights may be hung from a ceiling or an overhead surface and may hang over tables, desks, or other surfaces commonly occupied. Pendant lights are typically secured to an overhead surface by at least one cord, a chain, a line or rod and provide downward light distribution from an overhead position.

Ultra-violet light emitting bulbs, tubes, or LEDs may be used to kill germs and break down viruses in a number of applications by emitting radiation that is destructive to those bacteria and viruses. However, ultra-violet light can be hazardous to other types of life, including humans. Additionally, ultra-violet light is not visible, and therefore is not used in area lighting luminaires, even in cases that could benefit from both area lighting as well as the disinfecting properties of ultra-violet light.

SUMMARY

According to certain aspects, a luminaire includes an ultra-violet light emitter and is configured to emit ultra-violet light to an unoccupied portion of room.

According to certain aspects, a luminaire includes a housing having an upper portion and a lower portion. A wall is positioned between the upper portion and the lower portion. An upper channel is disposed in the upper portion and accommodating at least one ultra-violet light emitting low-pressure mercury discharge tube. A lower channel is disposed in the lower portion and accommodating at least one visible light emitting LED. The wall prevents transmission of ultra-violet light between the upper portion and the lower portion.

According to certain aspects, a luminaire includes a housing configured to be positioned over an area, the housing including a frame having a first channel for receiving a light emitter. A light emitter is positioned in the first channel. The light emitter is configured to emit ultra-violet light. A reflector assembly is connected to the frame to direct ultra-violet light emitted from the light emitter. At least a portion of the area is located at 0 degrees relative to the light emitter and a majority of the emitted ultra-violet light is emitted from the housing between 90 degrees and 130 degrees relative to the light emitter in a first direction.

According to certain aspects, a method of using ultra-violet light to disinfect an area includes providing a luminaire having a light emitter configured to emit ultra-violet light in a first direction and a controller operably connected to the light emitter. The luminaire is configured to be positioned over an area in a room. The controller is provisioned to activate the second light emitter based on a predetermined schedule. The predetermined schedule prevents an over-exposure condition for the area.

According to certain aspects, a luminaire includes a housing configured to be positioned over an area. The housing includes a frame. A light emitter is connected to the frame and configured to emit ultra-violet light. A reflector assembly is connected to the frame to direct ultra-violet light emitted from the light emitter. A controller includes an electronic processor and a memory. The controller is in communication with the light emitter and configured to control an on/off state and a duration of operation of the light emitter according to a scheduled irradiation scheme.

DETAILED DESCRIPTION

Figure 1:
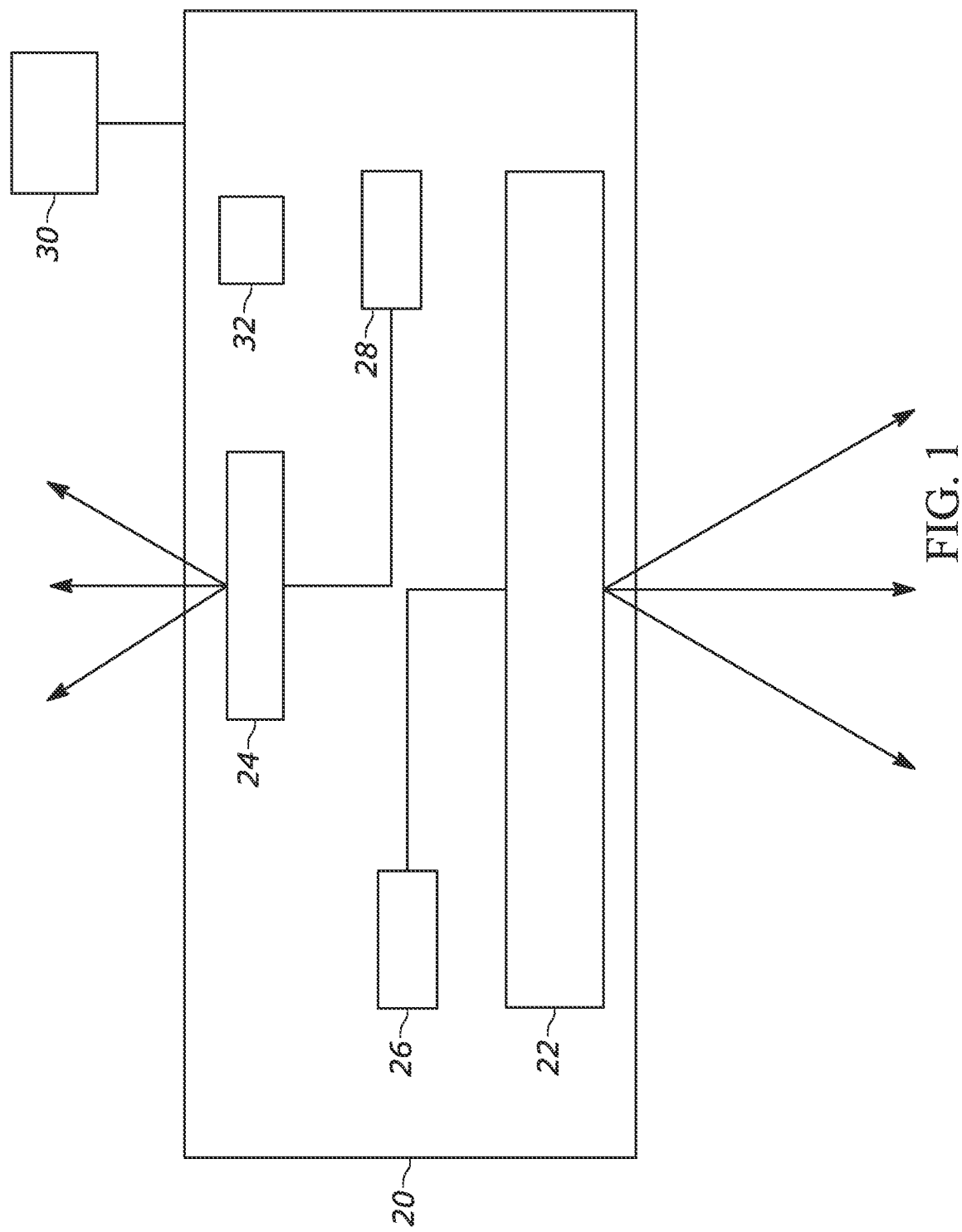
FIG. 1 is a schematic view of an exemplary light fixture including a UV light emitter.

Before any embodiments are explained in detail, it is to be understood that the embodiments are not limited to the details of construction and the arrangement of components set forth in the following description or illustrated in the following drawings. The various embodiments can be practiced or carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and may include electrical connections or couplings, whether direct or indirect. Also, electronic communications and notifications may be performed using any known means including wired connections, wireless connections, etc.

It should also be noted that a plurality of hardware and software based devices, as well as a plurality of different structural components may be used to implement the invention. In addition, it should be understood that embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software (for example, stored on non-transitory computer-readable medium) executable by one or more processors. As such, it should be noted that a plurality of hardware and software based devices, as well as a plurality of different structural components may be utilized to implement the invention. For example, "control units" and "controllers" described in the specification may include one or more electronic processors, one or more memory modules including non-transitory computer-readable medium, one or more input/output interfaces, and various connections (for example, a system bus) connecting the components.

Also, it is to be understood that the phraseology and terminology used herein are for the purpose of description and should not be regarded as limiting. The use of "including," "comprising," or "having" and variations thereof are meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. As used within this document, the word "or" may mean inclusive or. As a non-limiting example, if this document states "item z comprising element a or b," this may be interpreted to disclose an item z comprising only element a, an item z comprising only element b, as well as an item z comprising elements a and b.

For ease of description, some or all of the exemplary systems presented herein are illustrated with a single exemplar of each of its component parts. Some examples may not describe or illustrate all components of the systems. Other exemplary embodiments may include more or fewer of each of the illustrated components, may combine some components, or may include additional or alternative components.

Various exemplary embodiments of this application are directed to luminaire components that facilitate room disinfection by ultra-violet (UV) light emitted from a housing. In certain aspects the UV light can be directed to an upper portion of a room, for example an area above the position of an associated light fixtured. The luminaire can have both visible light emitters as well as UV light emitters. This application discusses components that can be used to provide adjustable ultra-violet light output as well as visual light output. The UV light can be used to kill or deactivate contaminants (e.g., viruses, bacteria, etc.) in an area, either on surfaces or in the air circulating in the area. Accordingly, the components and assemblies described herein can be integrated with other systems such as HVAC system, air filter systems, and the like.

FIG. 1 illustrates an exemplary schematic of a light fixture 20 having a first light emitter 22 and a second light emitter 24. The first light emitter 22 is configured to emit a first type of light, such as visible light in a first direction. The second light emitter 24 is configured to emit a second type of light, such as UV light (e.g., UV-C light) in a second direction. The first direction can be directed to an interior area, such as the floor of a room. The second direction can be directed in an opposite direction, such as a ceiling of a room. In this way the second light emitter 24 can be directed away from occupants in a room where the second type of light might be harmful to users.

A first power supply 26 provides power to the first light emitter 22 and a second power supply 28 provides power to the second light emitters 24. The first and second power supplies 26, 28 can be any combination of drivers, ballasts, or other power supply depending on the type of light emitters. For example, the first light emitter 22 can be light emitting diodes (LEDs) that utilize an LED driver as the power supply 26. The LED driver can be a separate component or can be integrated with a light engine on the same circuit board as the light emitters 22. The second light emitter 24 can be a UV bulb that utilizes a ballast as the second power supply 28. The first and second power supplies 26, 28 can be connected to line (aka, mains or building) power 30, for example through a junction box connection. In certain aspects, the light emitters 22, 24 can be connected to the same power supply or connected directly the line power 30.

One or more control components 32, can be connected to or integrated with the light fixture 20. The control components 32 can include backup battery units, fuses, surge protectors, wired or wireless communication modules (e.g., CAT5, radio, Wi-Fi, etc.), sensors (e.g., light, occupancy, motion, heat, temperature, etc.), or any combination thereof. The light fixture 20 can be connected to a network that includes other light fixtures and one or more controllers for distributed communication and centralized control of the light fixture.

Figure 2:
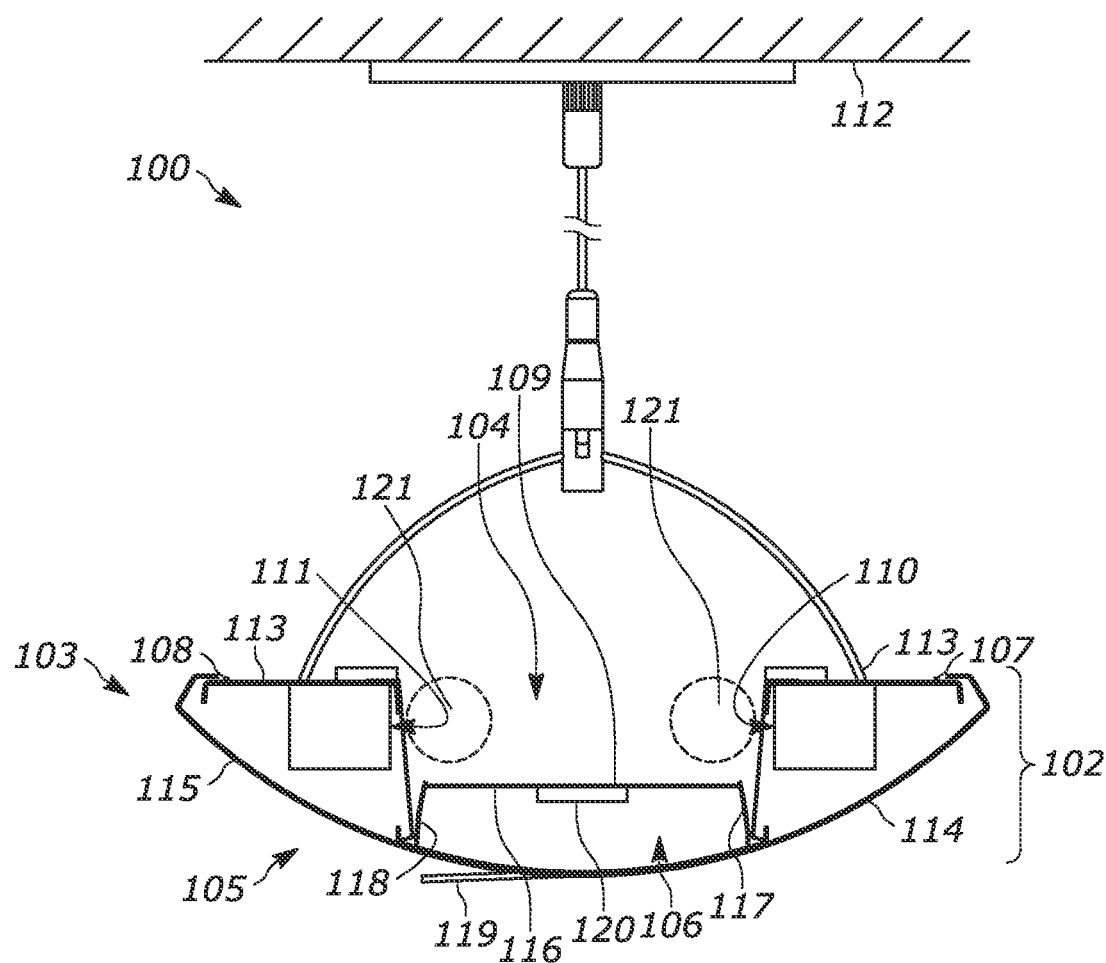
FIG. 2 is a sectional view of an exemplary pendant configuration for a luminaire including a UV uplight.

FIG. 2 illustrates a pendant luminaire 101 including a housing 102 having an upper portion 103 having an upper channel 104, and a lower portion 105 having a lower channel 106. The upper portion 103 also includes a first stepped-up 107 surface and a second stepped-up surface 108 on opposite sides of the upper channel 104. The stepped-up surfaces 107, 108 can extend along the sides of the upper channel 104, raised above a floor of the upper channel 109. The upper channel 104 is defined by a first upper side wall no, a second upper side wall in, and a recessed floor 109 extending between the first and second upper side walls 110, in. The first upper side wall 110 connects the first stepped-up surface 107 to the floor 109. Substantially parallel the first upper side wall no, and across the upper channel 104 from the first upper side wall 110, the second upper side wall 111 extends from the second stepped-up surface 108 to the floor 109. The upper channel 104 is configured to house and deliver power to an ultra-violet low-pressure mercury discharge tube 112. The first upper side wall no and the second upper side wall in may be substantially vertical when the pendant luminaire 101 is properly mounted to a ceiling surface 112.

One or more mounting components 113 can be disposed on at least one of the first stepped-up surface 107 and the second stepped-up surface 108 of the housing 102. The mounting components 113 are configured to secure the pendant luminaire 101 to a rod, a cord, a chain, or any other known component or assembly for hanging a luminaire from a ceiling surface. The mounting components 113 can also be configured to connect the housing 102 to a pole, post, ceiling, or other structure. Mounting components 113 may also include brackets having a pair of openings that receive fasteners to fasten the housing to a wall.

In the illustrated embodiment, the lower surface 105 has a curved configuration that can include a first arced surface 114 and second arced surface 115 on opposite sides of the lower channel 106. The arced surfaces can extend along the sides of the lower channel 106. Lower channel 106 is defined by a first lower wall 117, a second lower wall 118, and the upper mounting surface 116 of the lower channel 106. The first lower side wall 117 connects the first arced surface 114 to the upper mounting surface 116 of the lower channel 116. Substantially parallel the first lower side wall 117, and across the lower channel 106 from the first lower side wall 117, a second lower side wall 118 extends from the second arced surface 115 to the upper mounting surface 116 of the lower channel 106. A lens 119 is disposed between the first lower side wall 117 and the second lower side wall 118 and encloses the lower channel 106.

The lower channel 106 is configured to house at least one visible light emitter 120. For example, an incandescent bulb or a light emitting diode (LED) may be disposed on the upper mounting surface 116 of the lower channel 106. Additionally, the lower channel 106 can be configured to house one or more components that provide power to an incandescent light. For example, a circuit board can be positioned in the lower channel 106 that includes LEDs or a fitting or other connector can be provided for a bulb-type light emitter. The first lower side wall 117 and second lower side wall 118 may be substantially vertical when the pendant luminaire 101 is properly mounted to ceiling surface 112. A lens 119 is positioned over visible light emitter 120. The lens 119 can be plain or it can have optical features (e.g. frosting, textured surface, prisms, etc.) that alter or condition light emitted from the visible light emitter 120. The lens 119 can also be used to address color mixing or color angle concerns.

Housing 102 can be configured to receive one or more ultra-violet low-pressure mercury discharge tube 121 and one or more control components (not shown) for the ultra-violet low-pressure mercury discharge tube 121 (e.g. ballasts, drivers, fuses, surge protectors, sensors, communication modules, control modules). The luminaire 101 is configured to have a visible light output in a downward direction for example a direction opposite the upper mounting surface 116 of the lower channel 106. The luminaire is further configured to have an ultra-violet light output in an upward direction for example a direction opposite the floor of the upper channel 104. At least one of the surfaces defining the upper channel 104 and the lower channel 106 may include reflective surfaces, configured to further direct reflected ultra-violet light in an upward direction and reflected visible light in a downward direction.

The ultra-violet low-pressure mercury discharge tube 121 may be a UV bulb that emits UV-C light to inactivate bacteria, molds, viruses, or microbes present in water or air. The ultra-violet low-pressure mercury tube 121 may have a two pin base that fits into a socket disposed in or near the upper channel of the luminaire. The ultra-violet low-pressure mercury discharge tube 121 may draw power from the socket via the two pin base, and may emit radiation in the range of 100 nm<x<280 nm when powered. The "short" wavelengths emitted by the ultra-violet low-pressure mercury discharge tube 121 may be effective at altering the genetic composition of the microorganisms and render them harmless. The ultra-violet low-pressure mercury discharge tube 121 may also be dimmable or adjustable in intensity by use of electronic dimming controls.

As shown in FIG. 2, the housing 102 includes a lower channel 106 comprising an upper mounting surface 116 containing one or more visible light emitters 120, for example an LED. The visible light emitter 120 can be positioned on the upper mounting surface 116 or connected to a board (not shown), for example a printed circuit board (PCB) that is connected to the upper mounting surface 116. The light emitters 120 may be a plurality of light emitters, and the number and spacing of the light emitters can be altered to achieve a desired light output. The number, size, type, intensity, and configuration of the light emitters 120 can also be modified to achieve a desired light output. Different light emitter configurations can be provided on different PCB boards that are selectively attached to the flat upper mounting surface.

Figure 3:
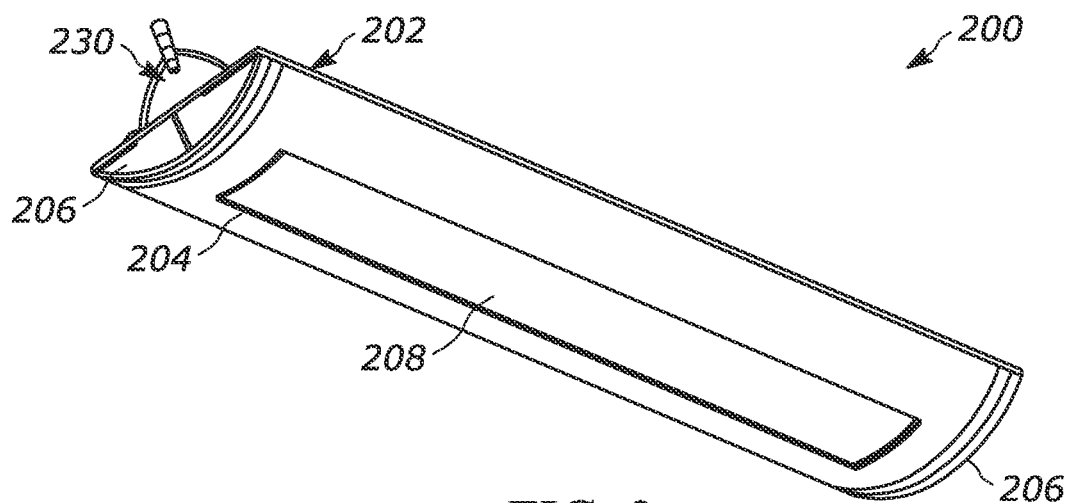
FIG. 3 is a perspective, bottom view of another exemplary configuration for a pendant luminaire including a UV uplight and a visible downlight.
Figure 4:
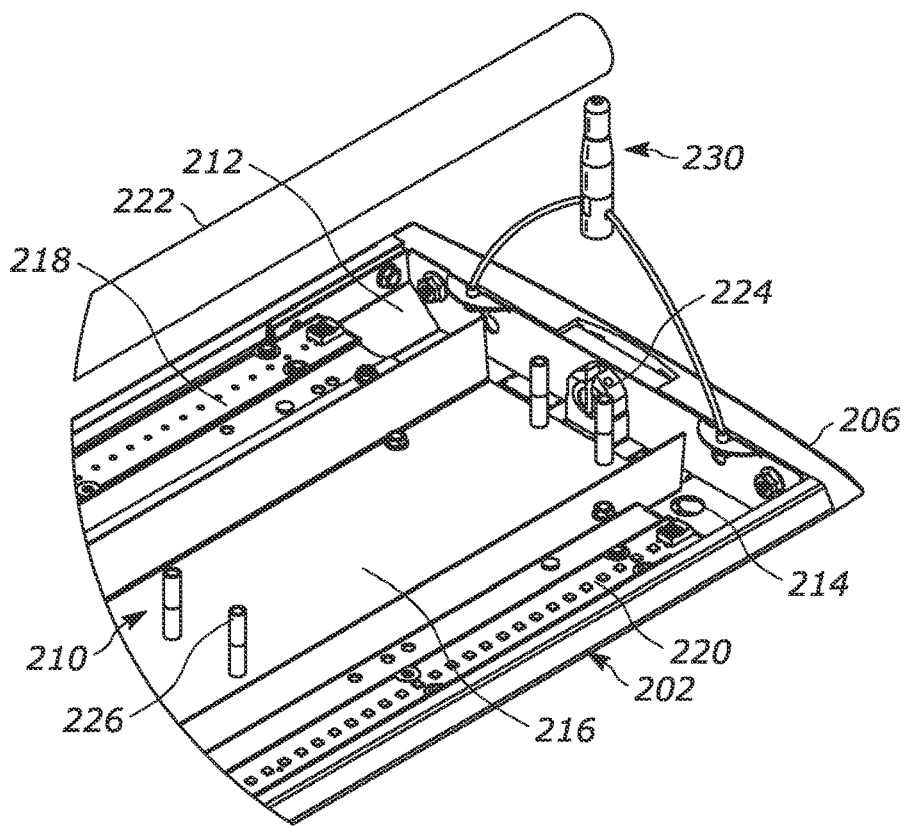
FIG. 4 is a partial top view of the pendant luminaire of FIG. 3.
Figure 5:
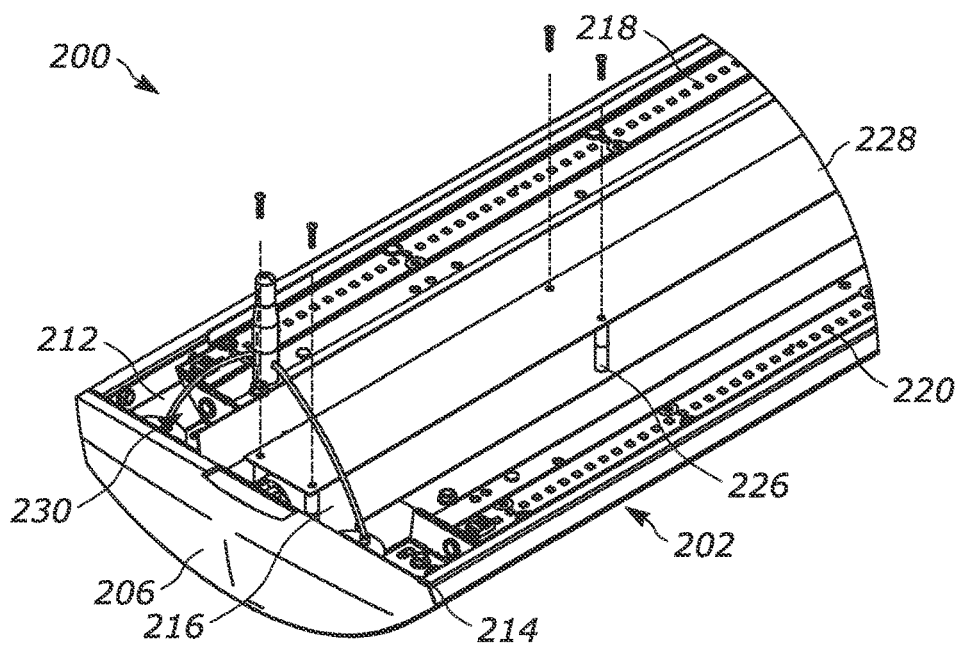
FIG. 5 is another partial top view of the pendant luminaire of FIG. 3

FIGS. 3-5 illustrates another luminaire configuration 200 including a housing 202 having a lower cover 204 and a pair of endcaps 206. The lower cover 204 includes an opening for a lens 208 to provide a downlight output. The lower cover 204 and the endcaps 206 are connected to a frame 210. The frame 210 can include one or more structural components allowing for the attachment of the outer housing components and internal electrical components such as light emitters and drivers. The luminaire 200 is configured to have a visible light output in a downward direction (downlighting), for example through the lens 208 toward a floor or other occupied area.

The frame 210 can include a lower channel configured to house at least one visible light emitter. For example, an incandescent bulb or a light emitting diode (LED) may be disposed in the lower channel. Additionally, the lower channel can be configured to house one or more components that provide power to the light. For example, a circuit board can be positioned in the lower channel that includes LEDs or a fitting or other connector can be provided for a bulb-type light emitter.

FIGS. 4 and 5 show an upper portion of the frame 210 that includes a first outer channel 212, a second outer channel 214, and an inner channel 216. Each of the outer channels 212, 214 and the inner channel 216 can have a substantially U-shaped configuration, with a bottom wall and respective side walls. One or more of the side walls may be shared between the channels. The walls of the channels can be reflective to disperse emitted light away from the frame 210.

The outer channels 212, 214 support one or more light emitters. For example, the first outer channel 212 can support a first set of LEDs 218 attached to a first PCB and the second outer channel 214 can support a second set of LEDs 220 attached to a second PCB. The first and second LEDs 218, 220 are oriented to emit visible light in an upward direction (uplighting), for example opposite the lens 208 or toward a ceiling of an occupied area. In certain embodiments, the luminaire 200 can be configured to provide both visual uplighting and downlighting as shown or can be configured to provide only visual uplighting or only visual downlighting.

Figure 6:
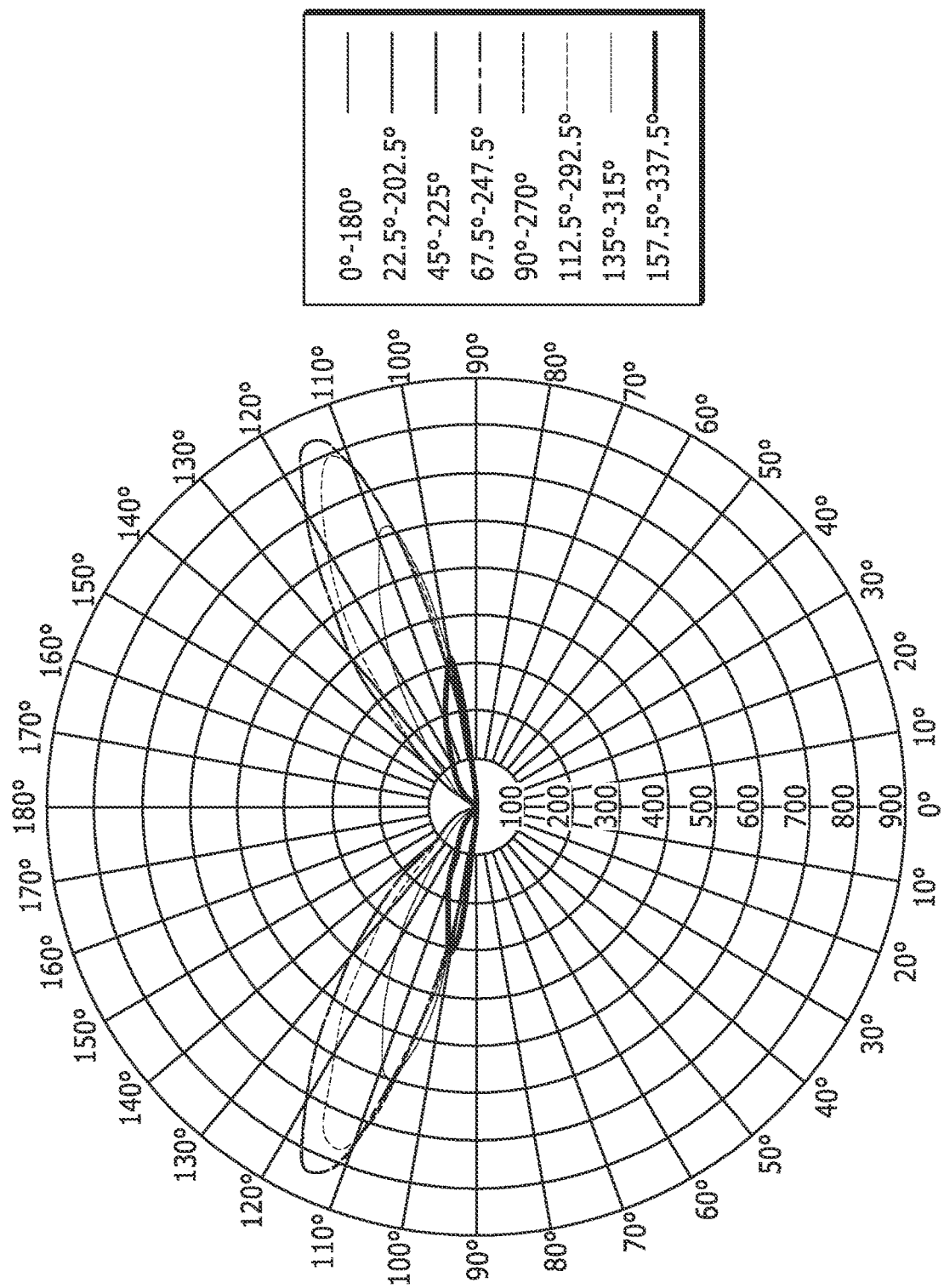
FIG. 6 is an exemplary light distribution graph for the luminaire of FIG. 3.

The housing 202 can also be configured to receive one or more non-visible light emitters. For example, the inner channel 216 can be configured to receive a UV light source 222 an provide UV lighting in an upward direction. The UV light source 222 can be a UV low-pressure mercury discharge tube. A pair of sockets 224 are provided in the inner channel 216 to receive and power the UV light source 222. One or more standoffs 226 extend from the bottom of the inner channel 216 to support a shield 228. The shield 228 can be connected to the standoffs 226 using a set of fasteners. The shield 228 acts to deflect and distribute the light emitter from the UV light source 222 away from the housing and out to the sides. FIG. 6 shows an example of the light distribution pattern for the UV light source 222. As shown, a majority of the light is emitted from the housing between 90 degrees and 130 degrees on either side in a butterfly wing light distribution.

The UV light source 222 can be configured to inactivate bacteria, molds, viruses, or microbes present in water or air. The UV light source 222 can draw power from the sockets 224 via a two pin base, and may emit radiation in the range of 100 nm<x<280 nm when powered. The "short" wavelengths emitted may be effective at altering the genetic composition of the microorganisms and render them harmless. The UV light source may be dimmable or adjustable in intensity by use of electronic dimming controls either through a manual operation or through automatic control. A controller can also be used to activate or deactivate the light source 222 under certain circumstances (such as occupancy events) or to cycle the light on and off under a controlled scheduled.

One or more mounting components can be connected to the frame 210 to support the housing 202 in a given location. For example, a yoke assembly 230 can be connected to each end of the frame 210 to support the housing 202 over a room.

An occupancy sensor may be connected to the frame 210 and operably connected to the visible light emitters and UV light source 222 to adjust the light output in response to a sensed occupancy of an area in which the luminaire 200 is installed. Control of at least one of the visible light emitters or the UV light source 222 may include switching on or off, dimming or brightening actions, or timer-based actions. For example, the occupancy sensor may sense that the area in which the luminaire 200 is installed is not occupied, and in response the electronic controls of the luminaire 200 may cause the UV light source 222 to switch on at a particular intensity, for preset time period. The preset time period may be selectable by a user of the luminaire 200 or may be based upon radiation exposure limit guidance correlated to the radiation output of the UV light source 222. The sensor can also be positioned and configured to address occupancy events positioned above a normal area, such as in the area of the UV emitted light. The luminaire 200 can be operated with other control components and under any control scheme described herein.

Figure 7:
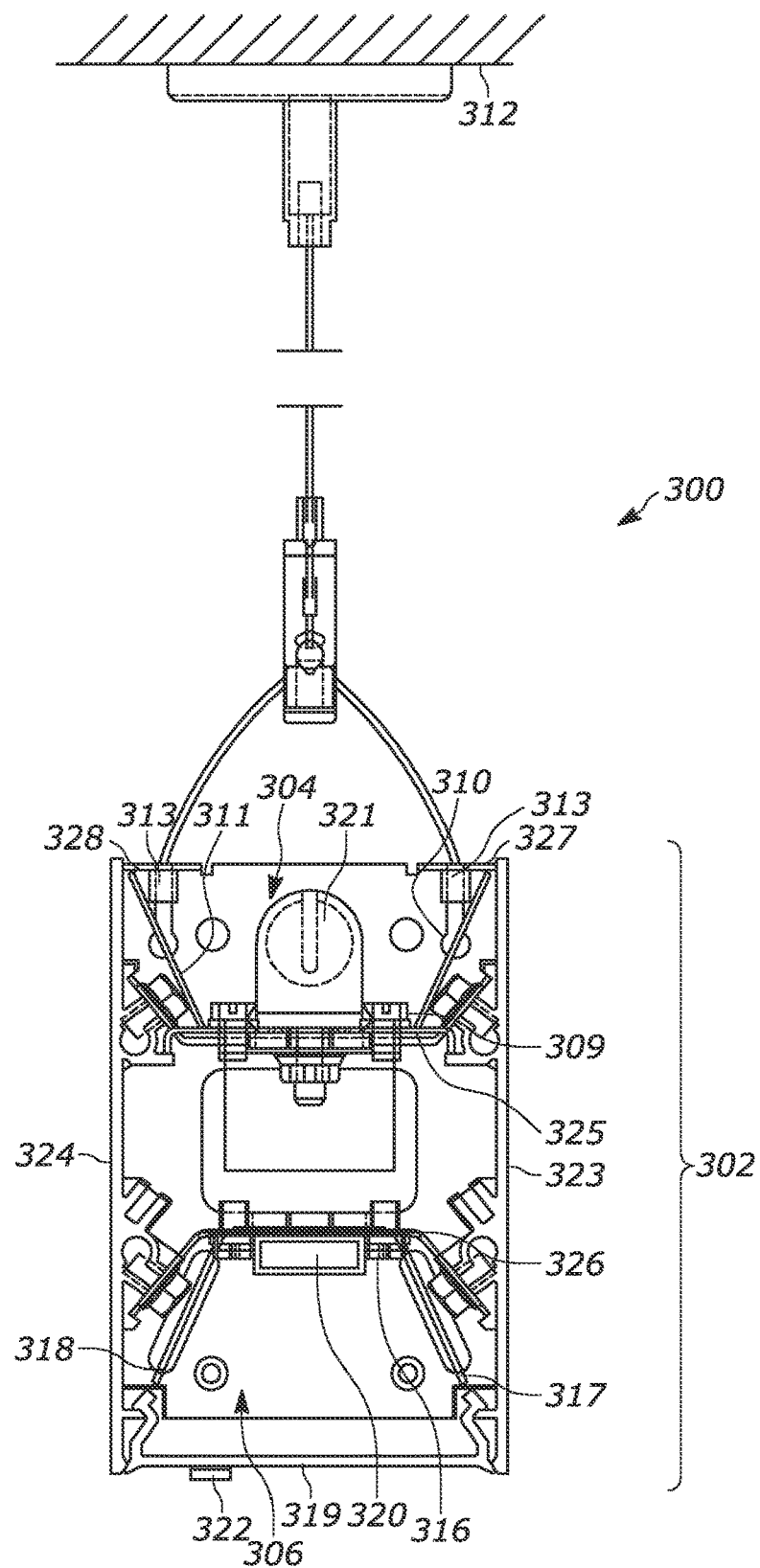
FIG. 7 is a sectional view of another exemplary luminaire including a UV uplight and visible downlight and having a pendant configuration.

FIG. 7 illustrates another luminaire 300 configured as a pendant fixture. The luminaire 300 includes a housing 302 defined by an upper channel 304, and a lower channel 306. The upper channel 304 is defined by a first upper side wall 310, a second upper side wall 311, and a floor 309. The first upper side wall 310 extends substantially vertically above the floor 309. Substantially parallel the first upper side wall 310, and across the upper channel 304 from the first upper side wall 310, a second upper side wall 311 extends substantially vertically from the floor channel 309. The upper channel 304 is configured to house and an ultra-violet low-pressure mercury discharge tube 321. The first upper side wall 310 and the second upper side wall 311 may be substantially vertical when the pendant luminaire 300 is properly mounted to a ceiling surface 312.

The lower channel 306 is defined by a first lower side wall 317, a second lower side wall 318, and an upper mounting surface. The first lower side wall 317 extends substantially vertically down from the floor of the lower channel 316. Substantially parallel to the first lower side wall 317, and across the lower channel 306 from the first lower side wall 317, the second lower side wall 318 extends vertically down from the upper surface of the lower channel 316. The lower channel 306 is configured to house and deliver power to a visible light emitter 320, for example, an LED, an incandescent bulb, or a fluorescent bulb. The first lower side wall 317 and second lower side wall 318 may be substantially vertical when the pendant luminaire is properly mounted to a surface 312.

A first housing side wall 323 extends between and connects the first upper side wall 310 to the first lower side wall 317. Similarly, a second housing side wall 324 extends between and connects the second upper side wall 311 to the second lower side wall 318. Electrical control components of the luminaire 300 may reside in an inner cavity defined by the first housing side wall 323 and the second housing side wall 324, as well as an upper inward surface 325 of the upper channel 304 and a lower inward surface 326 of the lower channel 306. For example, dimming or switching components may be disposed in cavity for controlling the light emission of at least one of the visible light emitters 320 disposed in the lower channel 306, or the ultra-violet low-pressure mercury discharge tube 321 disposed in the upper channel 309.

A first mounting flange 327 may extend horizontally from the first housing sidewall 323 over at least a portion of the upper channel 304, thereby partially enclosing the upper channel 304. Similarly, a second mounting flange 328 may extend from the second housing sidewall over at least a portion of the upper channel 304, thereby partially enclosing the upper channel 304. The second mounting flange 328 extends horizontally in an opposite direction of the first mounting flange 327.

Mounting components 313 are disposed on at least one of the first mounting flange 327 and the second flange 328. The mounting components 313 are configured to secure the pendant luminaire 300 to a rod, a cord, a chain, or any other known means for hanging a luminaire from a ceiling. The mounting components 313 can also be configured to connect the housing 302 to pole, post, ceiling, or other structure. The mounting components 313 may also be brackets comprising a pair of openings that receive fasteners to fasten the housing 302 to a wall instead of ceiling 312.

A lens 319 is disposed between the first lower side wall 317 and the second lower side wall 318, and encloses the lower channel 306. The lower channel 306 is configured to house at least one visible light emitter 320. For example, a fitting (not shown) for an incandescent bulb or an LED may be disposed on the flat upper mounting surface of the lower channel, and an incandescent bulb or LED may be connected thereto. First lower side wall 317 and second lower side wall 318 may be substantially vertical when the pendant luminaire 300 is properly hung from ceiling surface 312. Lens 319 is positioned below visible light emitter 320. The lens 319 can be plain or it can have optical features (e.g. frosting, textured surface, prisms, etc.) that alter or condition light emitted from the visible light emitter 320. The lens 319 can also be used to address color mixing or color angle concerns.

The housing 302 can be configured to receive one or more ultra-violet low-pressure mercury discharge tubes 321 and one or more control components (not shown) for the ultra-violet low-pressure mercury discharge tube 321 (e.g. ballasts, drivers, fuses, surge protectors, sensors, communication modules, control modules). The luminaire 300 is configured to have a visible light output in a downward direction for example a direction opposite the upper mounting surface 316 of the lower channel 306. The luminaire 300 is further configured to have an ultra-violet light output in an upward direction for example a direction opposite the floor 309 of the upper channel 304. At least one of the surfaces defining the upper channel 304 and the lower channel 306 may comprise reflective surfaces, configured to further direct reflected ultra-violet light in an upward direction and reflected visible light in a downward direction. An occupancy sensor 322 may be connected to the lens 319 to control at least one of the visible light emitters 320 or the ultra-violet low-pressure mercury discharge tube 321 in response to a sensed occupancy of an area in which the luminaire 300 is installed. Control of at least one of the visible light emitters 320 or the ultra-violet low-pressure mercury discharge tube 321 may comprising switching on or off, dimming or brightening actions, or timer-based actions. For example, the occupancy sensor 322 may sense that the area in which the luminaire 300 is installed is occupied and in response the electronic controls of the luminaire 300 may cause the ultra-violet low-pressure mercury discharge tube 321 to switch on at a particular intensity, for preset time period. The preset time period may be selectable by a user of the luminaire 300 or may be based upon radiation exposure limit guidance correlated to the radiation output of the ultra-violet low-pressure mercury discharge tube 321.

The ultra-violet low-pressure mercury discharge tube 321 may be a UV bulb that emits UV-C light to inactivate bacteria, molds, viruses, or microbes present in water or air. The ultra-violet low-pressure mercury tube 321 may have a two pin base that fits into a socket disposed in or near the upper channel of the luminaire. The low pressure-mercury discharge tube 321 may emit radiation in the range of 100 nm<x<280 nm. The "short" wavelengths emitted by the ultra-violet low-pressure mercury discharge tube 321 may be effective at altering the genetic composition of the microorganisms and render them harmless. The ultra-violet low-pressure mercury discharge tube 321 may also be dim-mable or adjustable in intensity by use of electronic dimming controls. The luminaire 300 can be operated with other control components and under any control scheme described herein.

Figure 8:
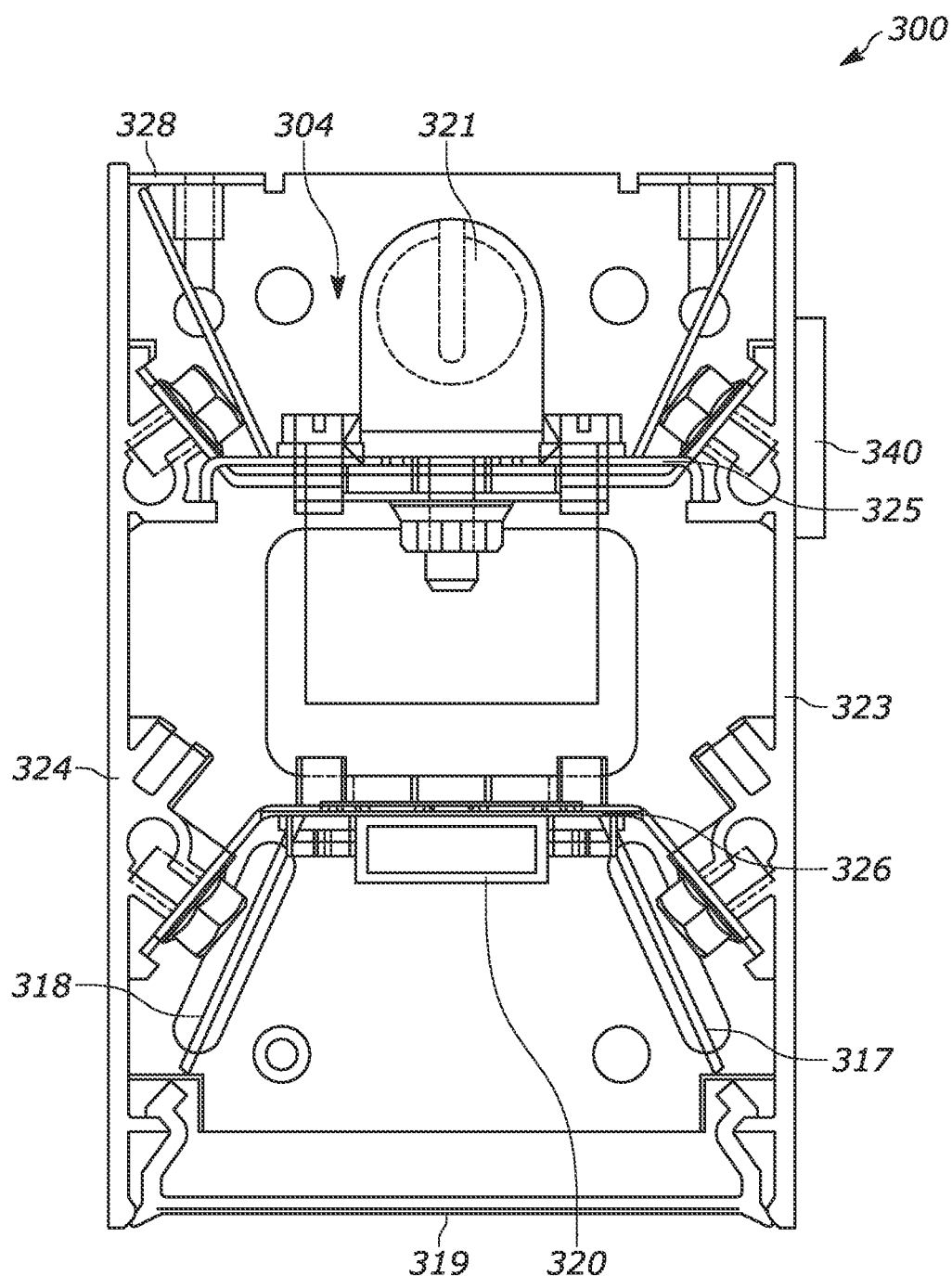
FIG. 8 is a sectional view of the luminaire of FIG. 7 having a wall mount configuration.

FIG. 8 shows the luminaire 300 of FIG. 7 in a wall-mountable configuration. At least one mounting component 340 is disposed on at least one of the first or second housing side walls 323, 324. The mounting component 340 may also include brackets comprising a pair of openings that receive fasteners to fasten the housing to a wall instead of a ceiling. This configuration allows the luminaire 300 to be mounted above an entryway, and exit, or door frame.

Figure 9:
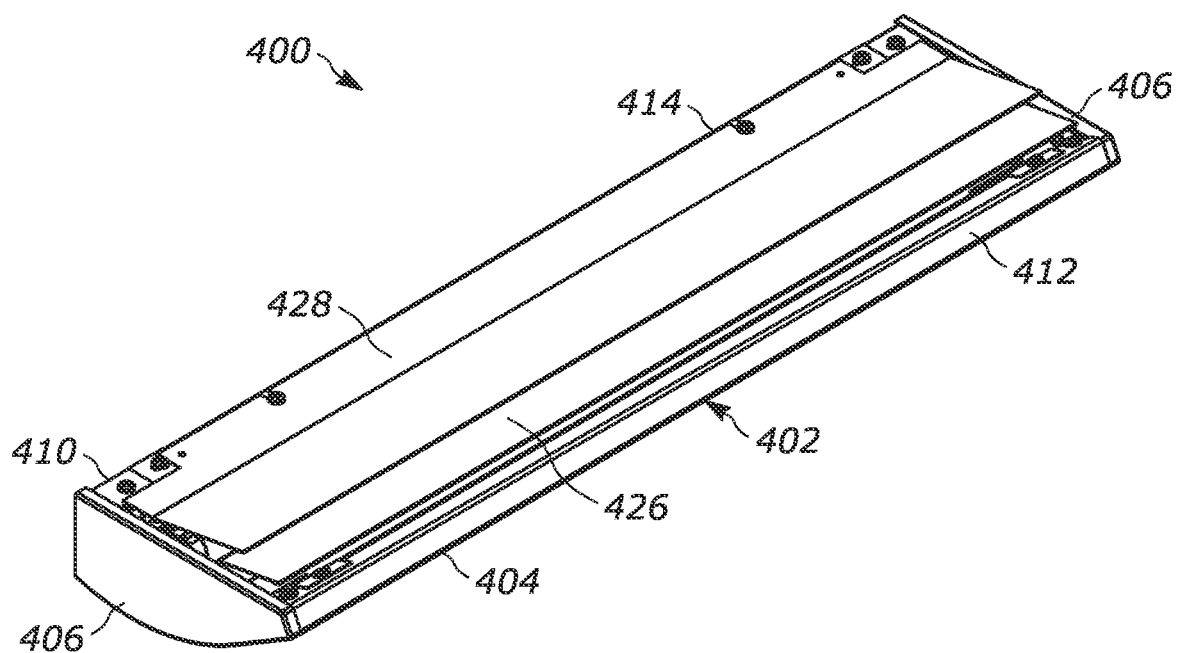
FIG. 9 is a perspective top view of an exemplary wall mount luminaire including a UV light emitter.
Figure 10:
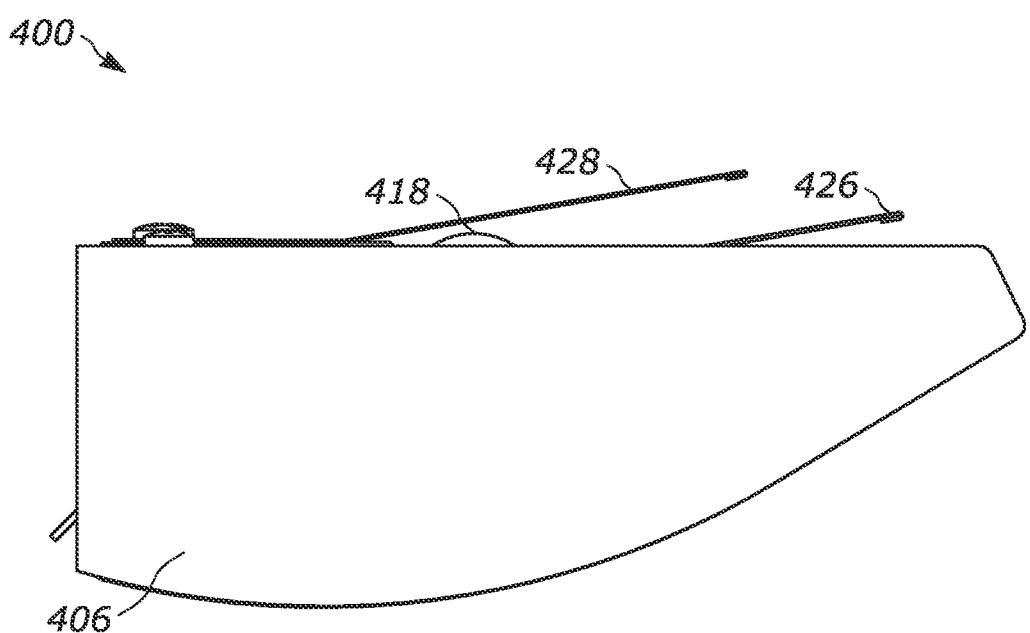
FIG. 10 is a side view of the luminaire of FIG. 9.
Figure 11:
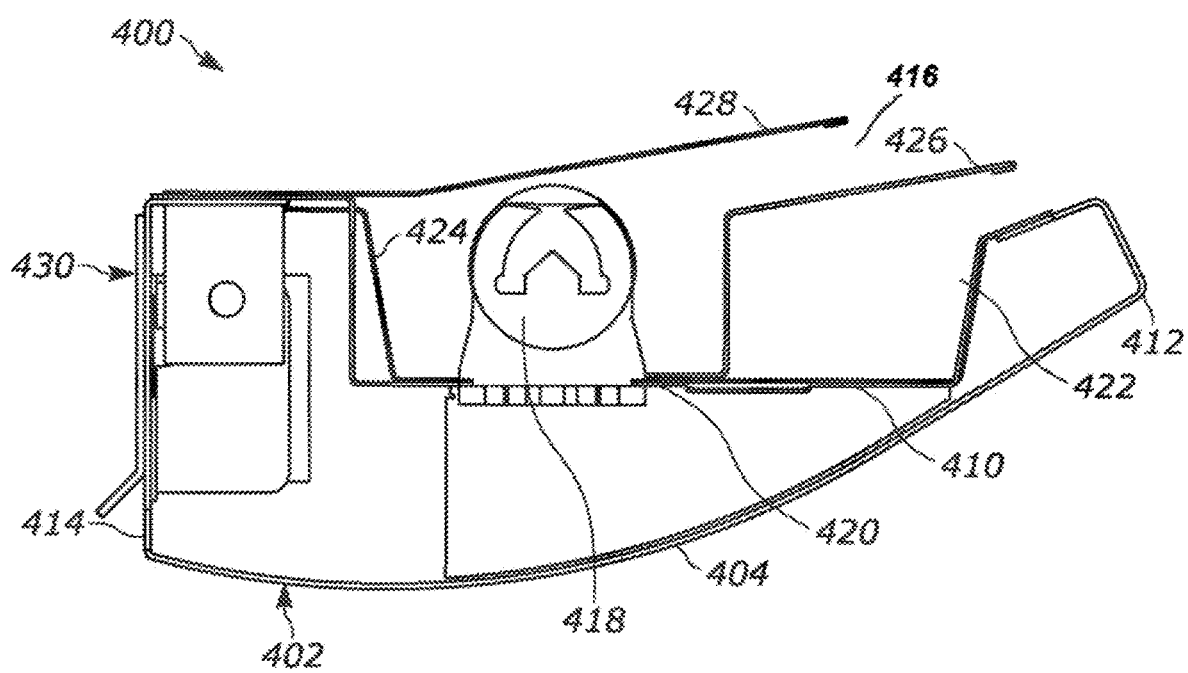
FIG. 11 is a sectional view of the luminaire of FIG. 9.

FIGS. 9-11 show another exemplary luminaire 400 including a housing 402 having a lower cover 404 and a pair of endcaps 406. The lower cover 404 and the endcaps 406 are connected to a frame 410. The frame 410 can include one or more structural components allowing for the attachment of the outer housing components and internal electrical components such as light emitters and drivers. The frame is configured to have an outer edge 412 that faces a room or other area and an inner edge 414 that faces a support, such as a wall.

FIG. 11 shows a side view of the frame 410 that includes a channel 416 for receiving a UV light source 418. The channel 416 can have a substantially U-shaped configuration, with a bottom wall 420, an outer side wall 422, and an inner side wall 424. The walls of the channel 416 can be reflective to disperse emitted light away from the frame 410.

The UV light source 418 can be a UV low-pressure mercury discharge tube. A pair of sockets are provided in the channel 416 to receive and power the UV light source 418. An outer reflector 426 and an inner reflector 428 are positioned on either side of the UL light source 418. The outer reflector 426 and the inner reflector 428 can be independently removable from the frame 410, for example using one or more fasteners. Removal of the reflectors 426, 428 can allow for the UV light source 418 to be easily changed and the light output adjusted.

Figure 12:
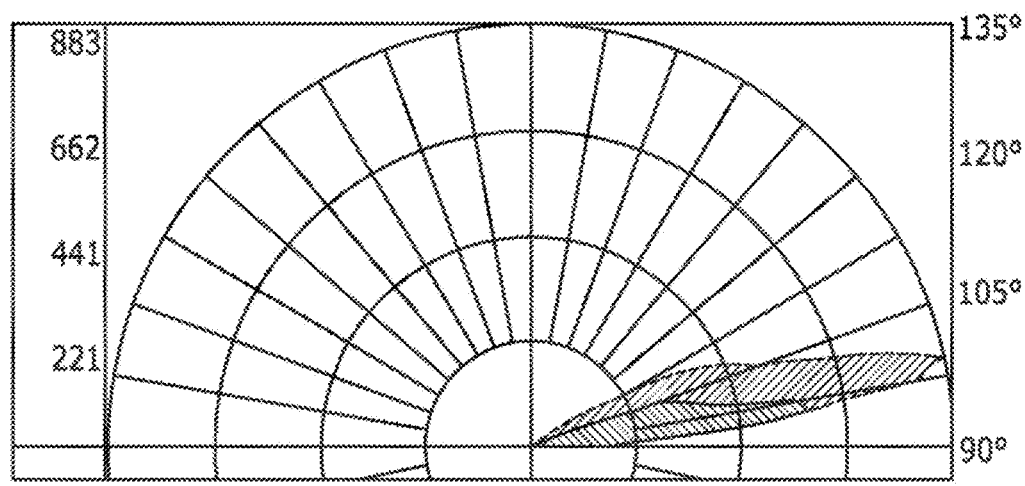
FIG. 12 is an exemplary light distribution graph for the luminaire of FIG. 9.

The outer reflector 426 has an S-shaped configuration with a lower portion engaging the bottom wall 420, a vertical portion extending from the lower portion, and an upper portion that extends at an angle from the vertical portion away from the bottom wall 420 and toward the outer edge 412 of the housing 402. The inner reflector 428 includes a first portion connected to the frame 410 and a second portion extending at an angle from the portion away from the bottom wall 420 and toward the outer edge 412 of the housing 402. The inner reflector can extend over the UV light source 418 and over at least part of the outer reflector 426. The outer reflector 426 and the inner reflector 428 direct the light outwardly away from the housing 402. FIG. 12 shows an exemplary light distribution for the UV light source 418 emitted from the housing 402. As shown in FIG. 12, the majority of light is emitted in a single direction between 90 degrees and 105 degrees.

The UV light source 418 can be configured to inactivate bacteria, molds, viruses, or microbes present in water or air. The UV light source 418 can emit radiation in the range of 100 nm<x<280 nm when powered. The "short" wavelengths emitted may be effective at altering the genetic composition of the microorganisms and render them harmless. The luminaire 400 can be operated with other control components and under any control scheme described herein.

One or more mounting components can be connected to the frame 410 to support the housing 402 in a given location.

For example, a wall bracket 430 can be connected to the frame 410 to support the housing 402 against a wall or other vertical support surface.

Figure 13:
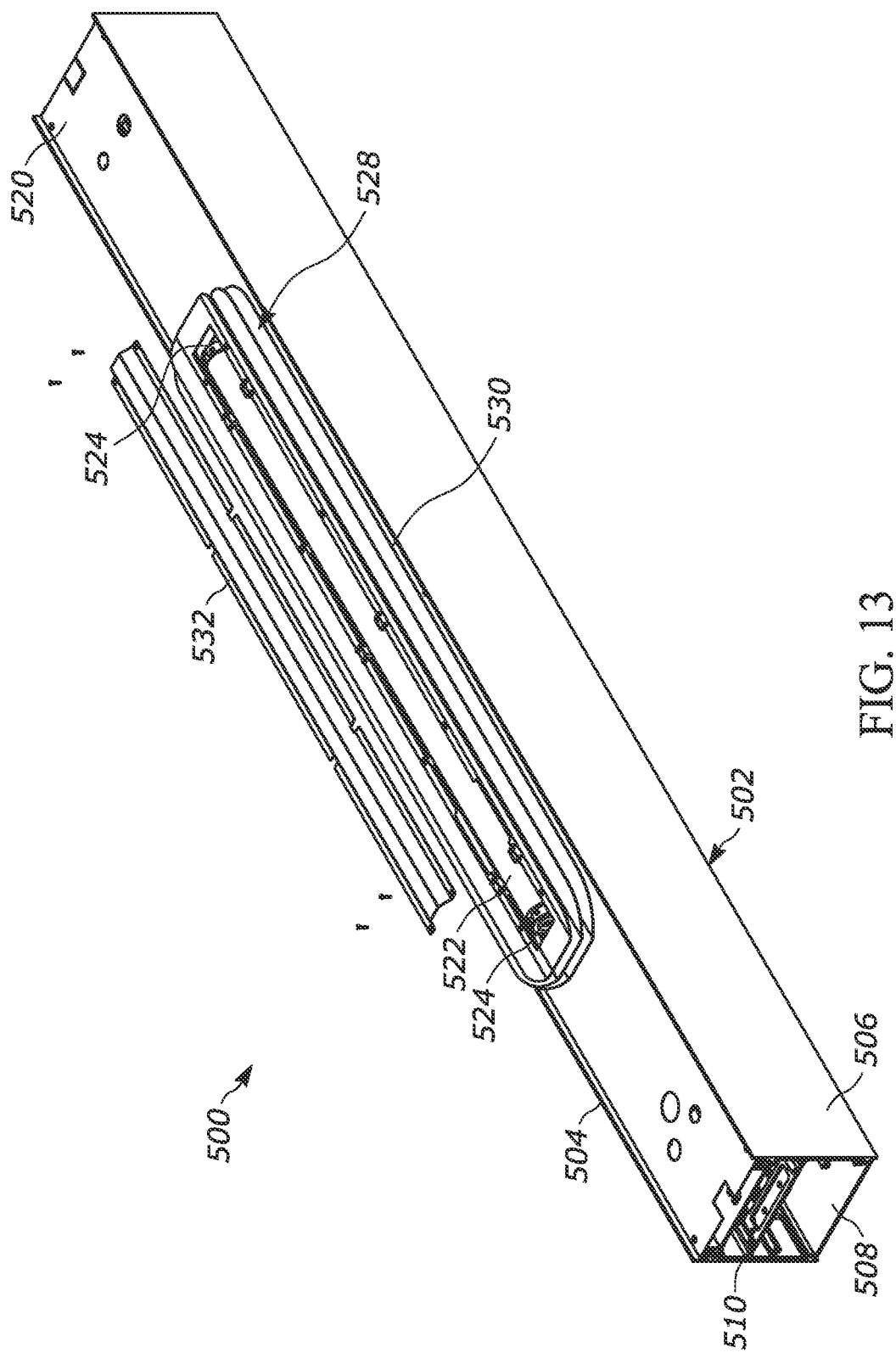
FIG. 13 is a perspective top view of an exemplary luminaire having a UV uplight and visible downlight.
Figure 14:
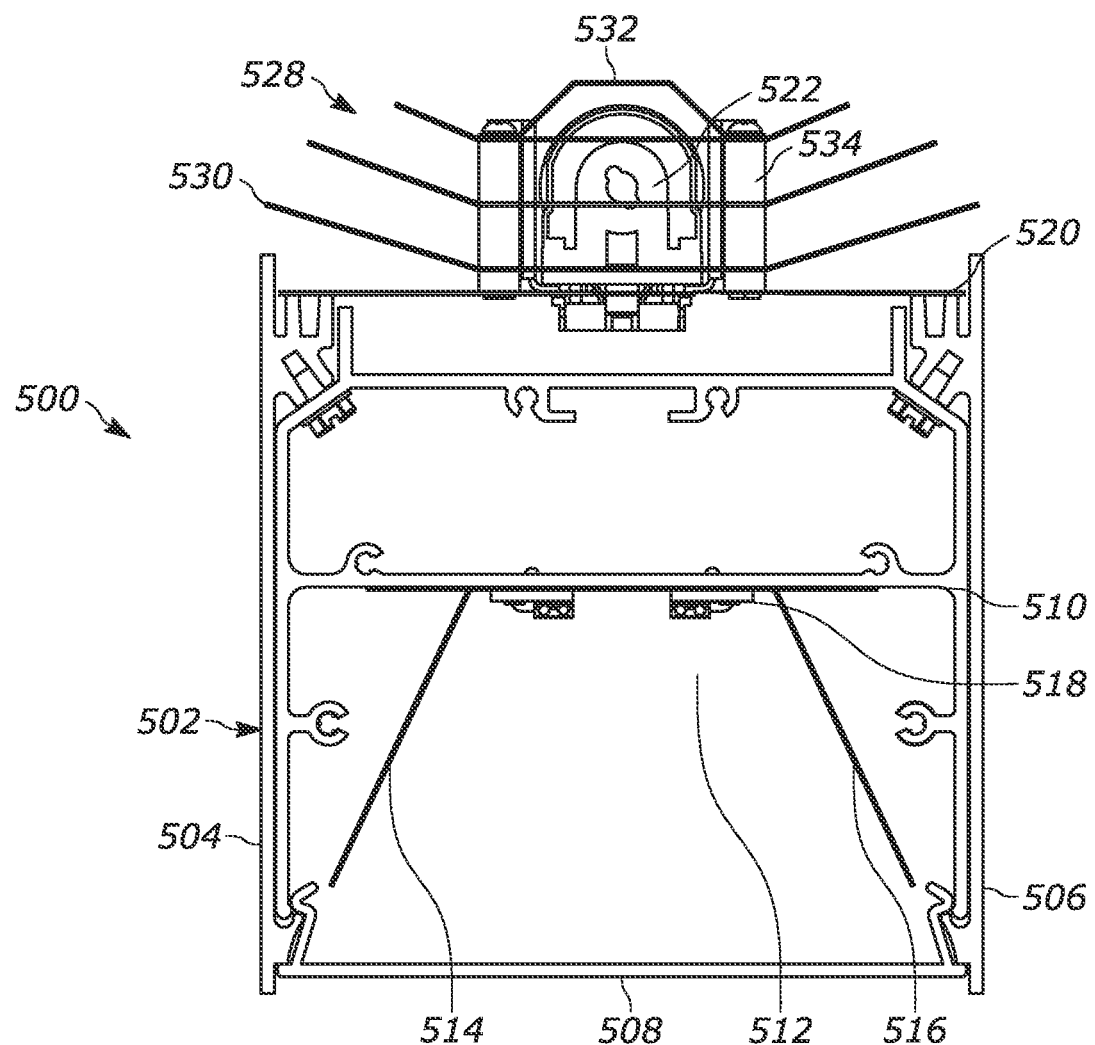
FIG. 14 is a sectional view of the luminaire of FIG. 13.

FIGS. 13 and 14 show another exemplary luminaire 500 including a housing 502 having a first side wall 504 and a second side wall 506. A pair of endcaps can be connected to either end of the side walls 504, 506. A lens 508 is connected to the side walls to provide a downlight output. The side walls 504, 506 are connected to a frame 510. The frame 210 can include one or more structural components allowing for the attachment of the outer housing components and internal electrical components such as light emitters and drivers.

The luminaire 500 is configured to have a visible light output in a downward direction (downlighting), for example through the lens 508 toward a floor or other occupied area. The frame 510 can include a lower channel 512 at least partially defined by a first reflector 514 and a second reflector 516. The lower channel 512 is configured to house at least one visible light emitter 518. For example, an incandescent bulb or one or more light emitting diodes (LED) can be disposed in the lower channel 512. Additionally, the lower channel 512 can be configured to house one or more components that provide power to the light. For example, a circuit board can be positioned in the lower channel that includes LEDs or a fitting or other connector can be provided for a bulb-type light emitter.

An upper cover 520 can be connected to the first and second side walls 504, 506 and a UV light source 522 can extend from the upper cover 520. The UV light source 522 can be a UV low-pressure mercury discharge tube. A pair of sockets 524 are provided to receive and power the UV light source 522. The UV light source 522 can be configured to inactivate bacteria, molds, viruses, or microbes present in water or air. The UV light source 522 can draw power from the sockets 524 via a two pin base, and may emit radiation in the range of 100 nm<x<280 nm when powered. The "short" wavelengths emitted may be effective at altering the genetic composition of the microorganisms and render them harmless. The luminaire 500 can be operated with any control components and under any control scheme described herein.

The luminaire 500 can include a series of baffles 528 that are positioned around the UV light source 522. The one or more baffles 528 are configured to direct at least a portion of the light emitted from the UV light source 522. For example, the baffles 528 can be configured to direct light laterally relative to the housing 502 and upwardly relative to the housing 502. The baffles 528 can include reflective surfaces, e.g., mirrored surfaces.

Figure 15:
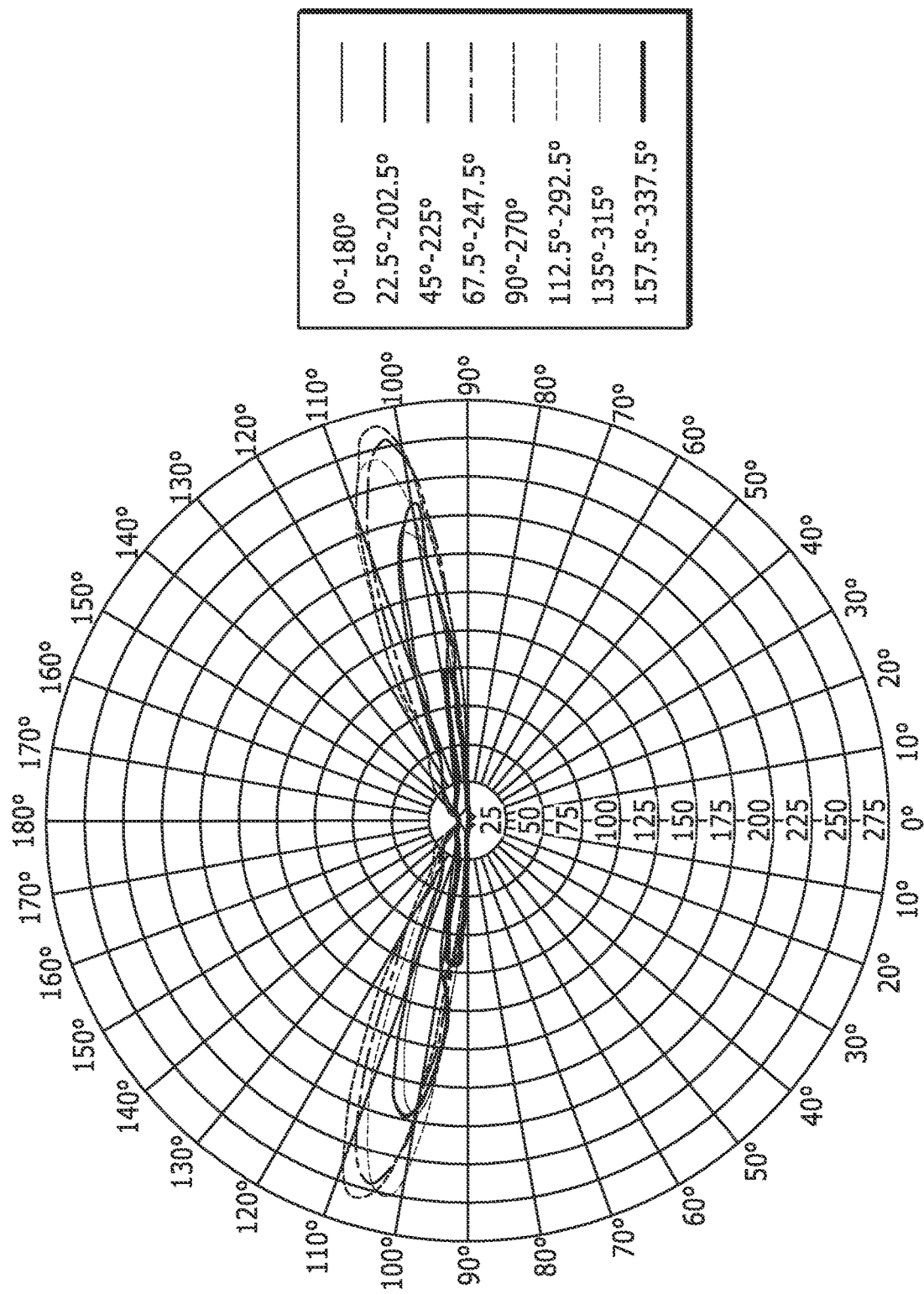
FIG. 15 is an exemplary light distribution graph for the luminaire of FIG. 13.

In an exemplary embodiment, the baffles 528 include a set of lower baffles 530 that surround the sides of the UV light source 522 and an upper baffle 532 that is removably connected to the lower baffles 530. The lower baffles 530 include a first portion extending latterly from the UV light source 522 and a second portion extending at an oblique angle outwardly and upwardly from the UV light source 522 relative to the housing 502. The upper baffle 532 can cover the entire top surface of the UV light source 522. The upper baffle 532 can be releasable connected to one or more posts 534, so that removal of the upper baffle 532 allows for replacement of the UV light source 522. FIG. 15 shows an example of the light distribution pattern for the UV light source 522. As shown, a majority of the light is emitted from the housing between 90 degrees and 120 degrees on either side in a butterfly wing light distribution.

Figure 16:
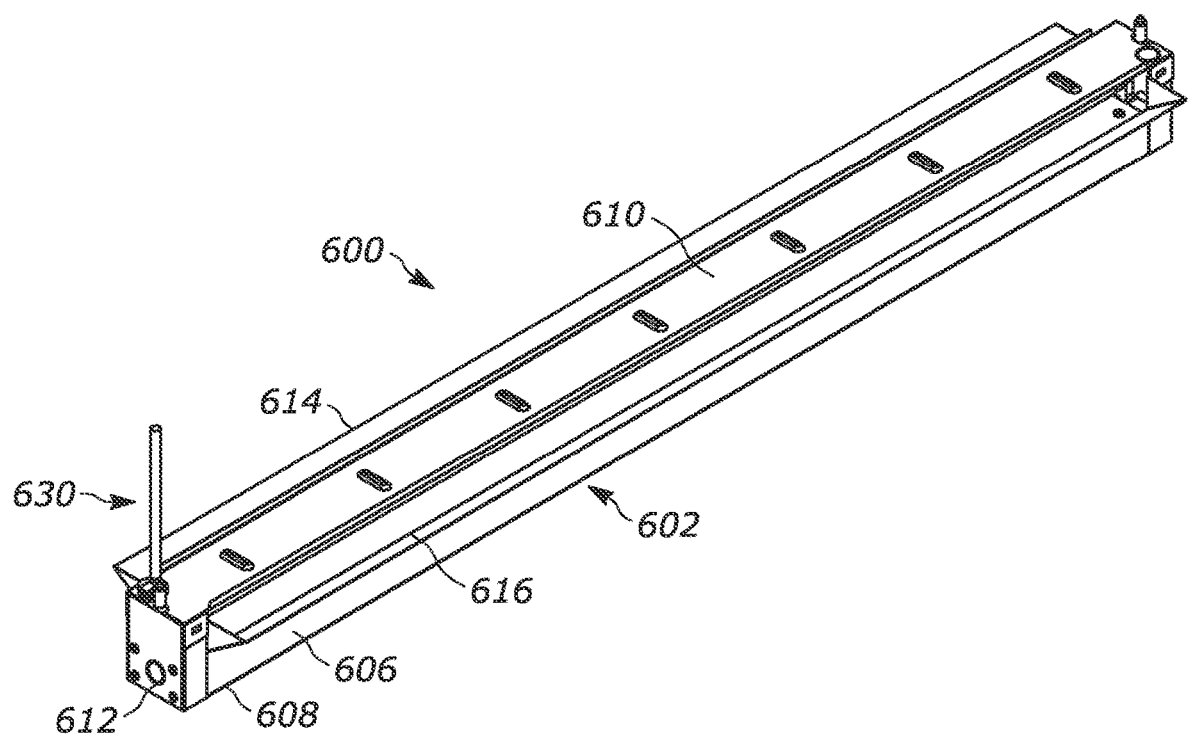
FIG. 16 is a perspective top view of an exemplary luminaire including a UV uplight.
Figure 17:
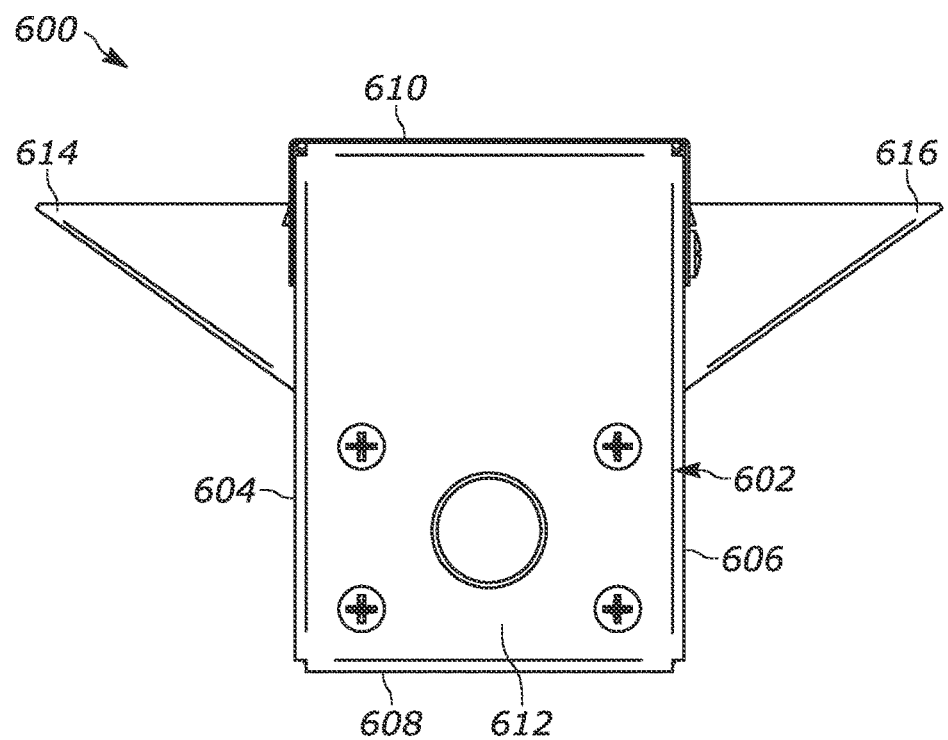
FIG. 17 is a side view of the luminaire of FIG. 16.
Figure 18:
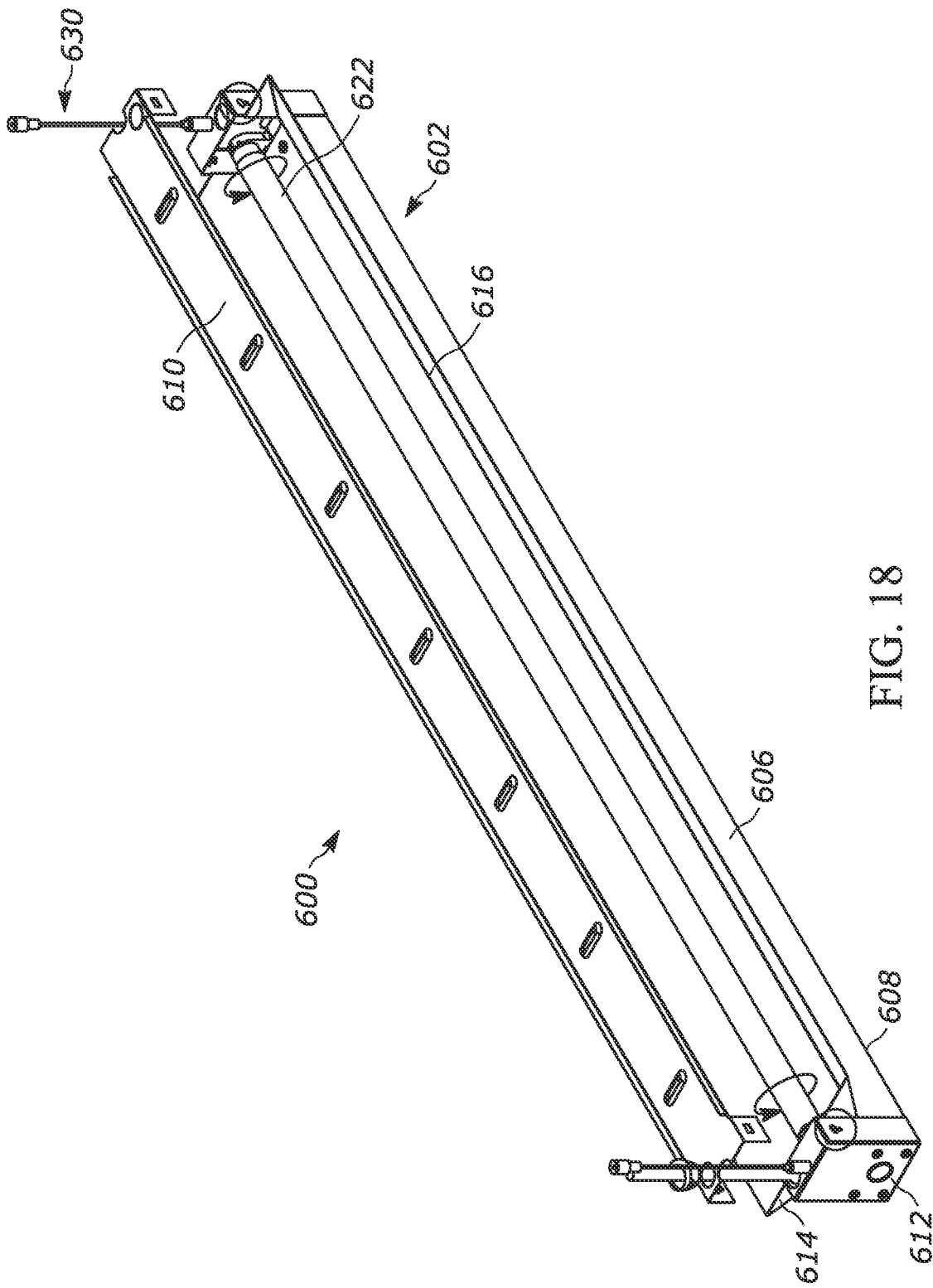
FIG. 18 is a perspective top view of the luminaire of FIG. 16, with the upper cover removed.

FIGS. 16-18 show another exemplary luminaire 600 including a housing 602 having a first side wall 604, a second side wall 606, a lower wall 608, and an upper cover 610. The upper cover 610 can be removably connected to the side walls 604, 606. A pair of endcaps 612 can be connected to either end of the side walls 604, 606.

A UV light source 622 can be positioned in the housing 602. The UV light source 622 can be a UV low-pressure mercury discharge tube. A pair of sockets are provided to receive and power the UV light source 622. The UV light source 622 can be configured to inactivate bacteria, molds, viruses, or microbes present in water or air. The UV light source 622 can draw power from the sockets via a two pin base, and may emit radiation in the range of 100 nm<x<280 nm when powered. The "short" wavelengths emitted may be effective at altering the genetic composition of the microorganisms and render them harmless. The luminaire 600 can be operated with any control components and under any control scheme described herein.

Figure 19:
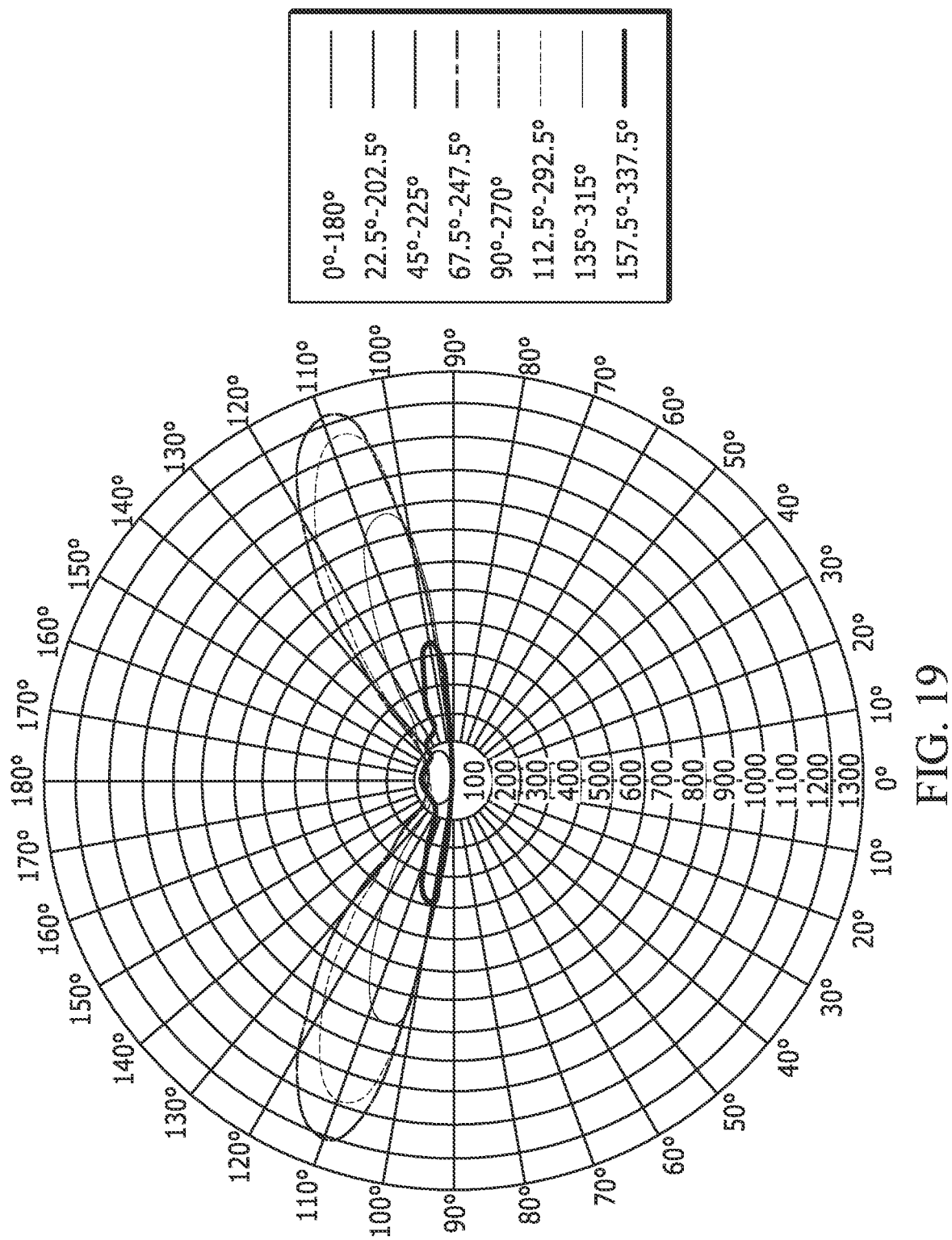
FIG. 19 is an exemplary light distribution graph for the luminaire of FIG. 18.

The first side wall 604 includes a lower vertical portion and a first reflector portion 614 extending outwardly at an oblique angle from the vertical portion. Similarly, the second side wall 606 includes a lower vertical portion and a second reflector portion 616 extending outwardly at an oblique angle from the vertical portion. The first and second reflector portions 614, 616 have a substantially triangular configuration. The upper cover 610 is removably connected over the UV light source 622 to allow for replacement of the unit or bulb. The reflectors and the cover combine to direct the UV light output upward and away from the housing. FIG. 19 shows an example of the light distribution pattern for the UV light source 622. As shown, a majority of the light is emitted from the housing between 90 degrees and 130 degrees on either side in a butterfly wing light distribution.

One or more mounting components can be connected to the housing 602 to support the housing 602 in a given location. For example, a cable assembly 630 can be connected to each of the endcaps 612 to support the housing 602 over a room.

Figure 20:
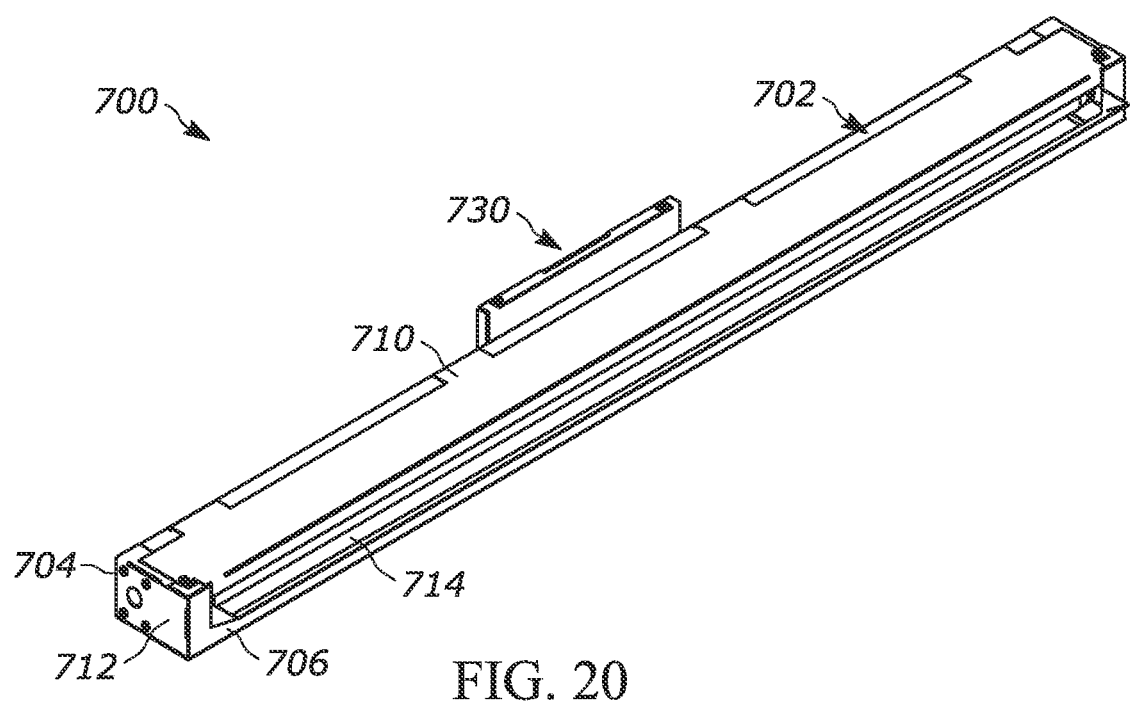
FIG. 20 is a perspective top view of an exemplary luminaire having a UV uplight.
Figure 21:
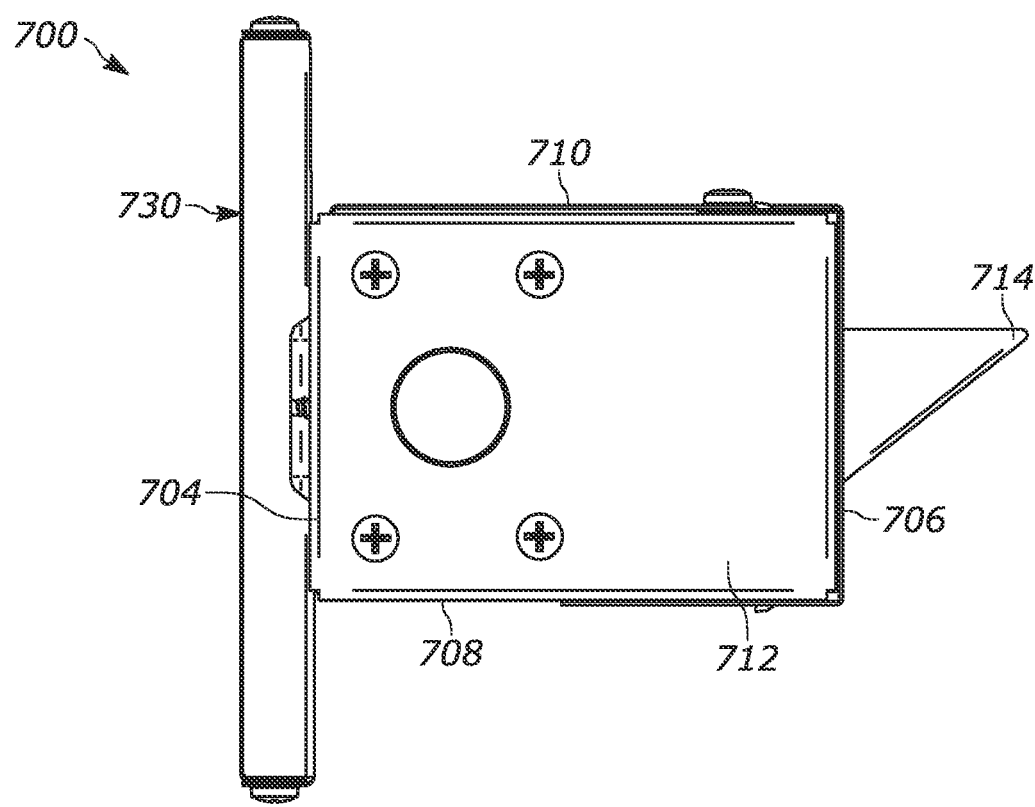
FIG. 21 is a side view of the luminaire of FIG. 20.
Figure 22:
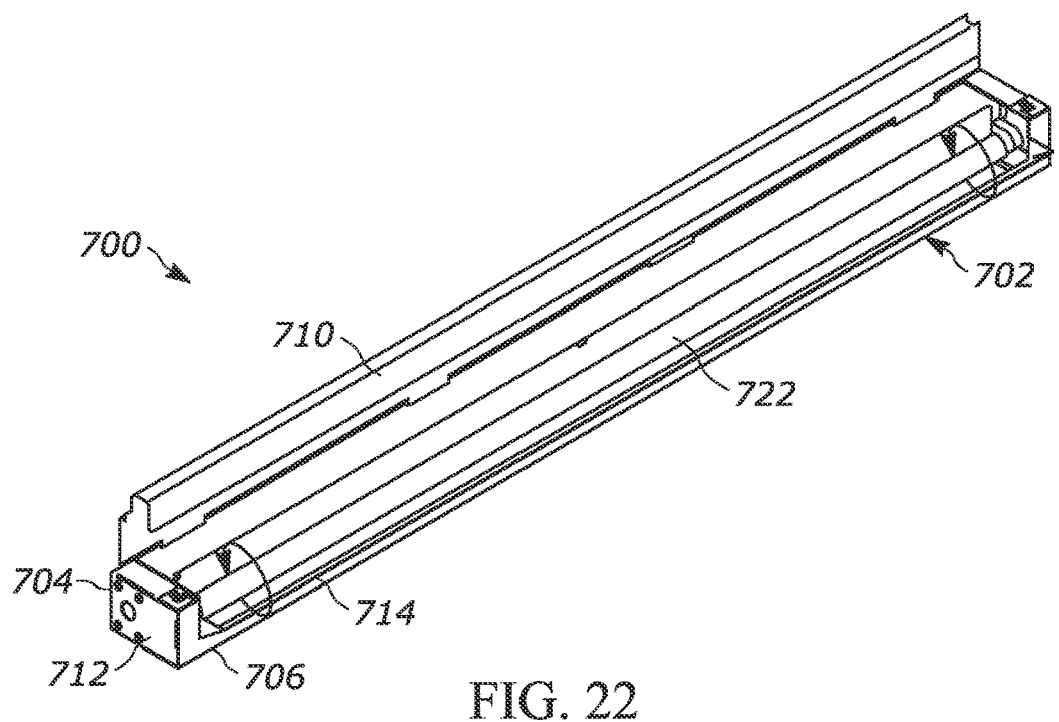
FIG. 22 is a perspective top view of the luminaire of FIG. 20 with the upper cover pivoted to an open position.

FIGS. 20-22 show another exemplary luminaire 700 including a housing 702 having a first side wall 704, a second side wall 706, a lower wall 708, and an upper cover 710. The upper cover 710 can be pivotally connected to the first side wall 704. A pair of endcaps 712 can be connected to either end of the side walls 704, 706.

A UV light source 722 can be positioned in the housing 702. The UV light source 722 can be a UV low-pressure mercury discharge tube. A pair of sockets are provided to receive and power the UV light source 722. The UV light source 722 can be configured to inactivate bacteria, molds, viruses, or microbes present in water or air. The UV light source 722 can draw power from the sockets via a two pin base, and may emit radiation in the range of 100 nm<x<280 nm when powered. The "short" wavelengths emitted may be effective at altering the genetic composition of the microorganisms and render them harmless. The luminaire 700 can be operated with any control components and under any control scheme described herein.

Figure 23:
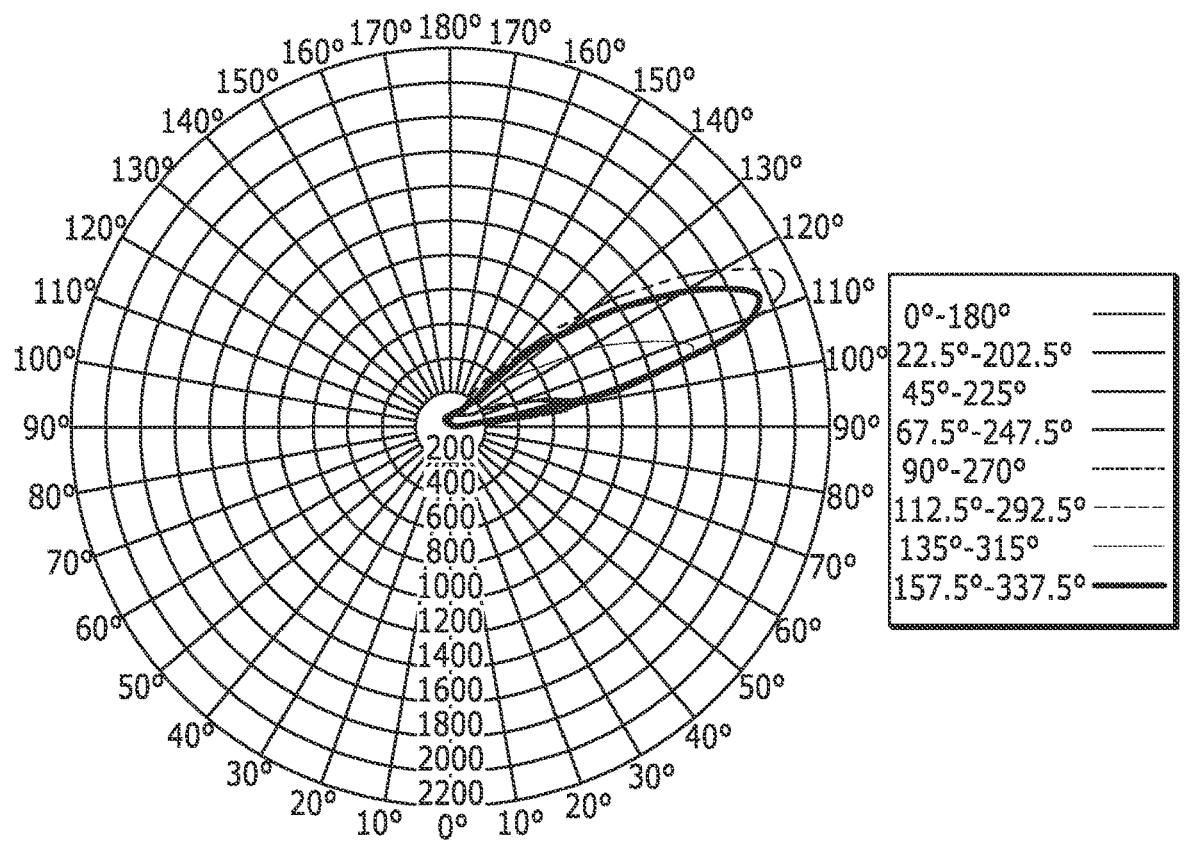
FIG. 23 is an exemplary light distribution graph for the luminaire of FIG. 21.

The second side wall 606 includes a lower vertical portion and a reflector portion 714 extending outwardly at an oblique angle from the vertical portion. The reflector portion 714 has a substantially triangular configuration. The upper cover 710 is movably connected over the UV light source 722 to allow for replacement of the unit or bulb. The reflector and the cover combine to direct the UV light output upward and away from the housing. FIG. 23 shows an example of the light distribution pattern for the UV light source 722. As shown, a majority of the light is emitted from the housing between 100 degrees and 130 degrees on one side of the housing 702.

One or more mounting components can be connected to the housing 702 to support the housing 702 in a given location. For example, a wall bracket 730 can be connected to the first wall 704 to support the housing 702 against a wall or other vertical support surface.

The luminaires described herein may be used in combination with a fan, blower, or any other gas or liquid circulator to facilitate the movement of contaminated air or liquid in front of the ultra-violet low-pressure mercury discharge tube to be decontaminated. In some embodiments, a gas or liquid circulator may be disposed in the housing and circulate air through the housing and in front of the ultra-violet low-pressure mercury discharge tube.

In certain aspects a light fixture is configured to decontaminate air as it flows through a housing. A light fixture can include one or more light emitters that are positioned in an airflow channel and emit light (e.g., UV light) into the channel to decontaminate air as it passes through the housing. Airflow can be provided by natural convection or through forced movement. Forced movement can be provided by a mechanical device (e.g., a fan) that is positioned inside the light fixture or positioned external to the light fixture. For example, the light fixture can include one or more ducts that connect to a forced airflow conduit. The airflow can be part of a buildings ventilation system, and air movement can be created by one or more fans positioned at a remote location.

Figure 24:
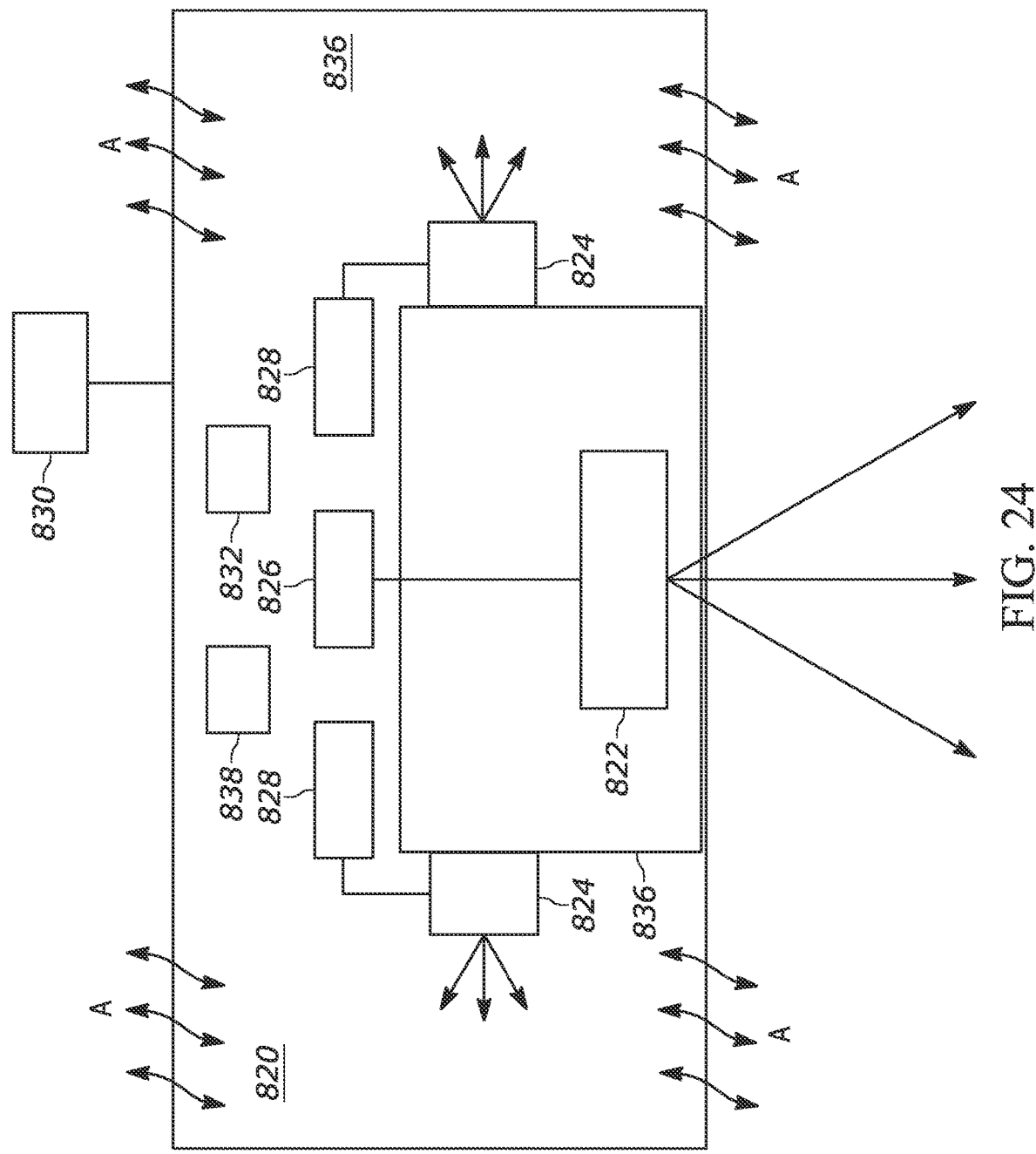
FIG. 24 is a schematic view of a light fixture incorporating an air mover and interior germicidal light emitter.

FIG. 24 illustrates an exemplary schematic of a light fixture 820 having a first light emitter 822 and a second light emitter 824. The first light emitter 822 is positioned in an inner housing 834 and configured to emit a first type of light, such as visible light in a first direction. The second light emitter 824 is positioned in an outer housing 836 and configured to emit a second type of light, such as UV light (e.g., UV-C light) in a second direction. The first direction can be directed to an interior area, such as the floor of a room. The second direction can be directed into the outer housing 836. The outer housing 836 is further configured to permit airflow A through the light fixture 820. This can include vents, channels, conduits, and/or baffles to permit and direct airflow through the light fixture in a controlled manner so that air is decontaminated by the second light emitters 824. While two second light emitters 824 are shown, the number of second light emitters 824 can depend on the configuration of the light fixture 820 and the outer housing 836.

A first power supply 826 provides power to the first light emitter 822 and a second power supply 828 provides power to the second light emitters 824. The first and second power supplies 826, 828 can be any combination of drivers, ballasts, or other power supply depending on the type of light emitters. For example, the first light emitter 822 can be light emitting diodes (LEDs) that utilize an LED driver as the power supply 826. The LED driver can be a separate component or can be integrated with a light engine on the same circuit board as the light emitters 822. The second light emitter 824 can be a UV bulb that utilizes a ballast as the second power supply 828. The first and second power supplies 826, 828 can be connected to line (aka, mains or building) power 830, for example through a junction box connection. In certain aspects, the light emitters 822, 824 can be connected to the same power supply or connected directly the line power 830.

One or more control components 832, can be connected to or integrated with the light fixture 820. The control components 832 can include backup battery units, fuses, microprocessors, FPGAs, surge protectors, wired or wireless communication modules (e.g., CAT5, radio, WiFi, etc.), sensors (e.g., light, occupancy, motion, heat, temperature, etc.), or any combination thereof. The light fixture 820 can be connected to a network that includes other light fixtures and one or more controllers for distributed communication and centralized control of the light fixture.

The light fixture 820 can also be associated with an air mover 838 (e.g., fan, blower, etc.). The air mover 838 can be positioned inside of the light fixture 820 and assists in circulating air through the outer housing 836 so that it can be decontaminated by the second light emitters 824. Airflow A can be in any direction through the light fixture 820. Although depicted as moving through either the top or bottom of the outer housing 836, air can also be circulated through the sides. The position of the light emitters 822, 824 can also be adjusted based on the configuration of the light fixture 820, the desired light output, and the desired airflow characteristics.

In certain aspects, the air mover 838 can be positioned remotely from the light fixture 820 and the outer housing 836 can be configured to be in fluid communication with the external air mover 838. For example, the outer housing 836 can include one or more conduits or ducts that are configured to fluidly connect the light fixture 820 with a ventilation system. An example of light fixture that incorporates a ventilation connection is described in U.S. Pat. No. 7,384, 168, the disclosure of which is herein incorporated by reference in its entirety.

Figure 25:
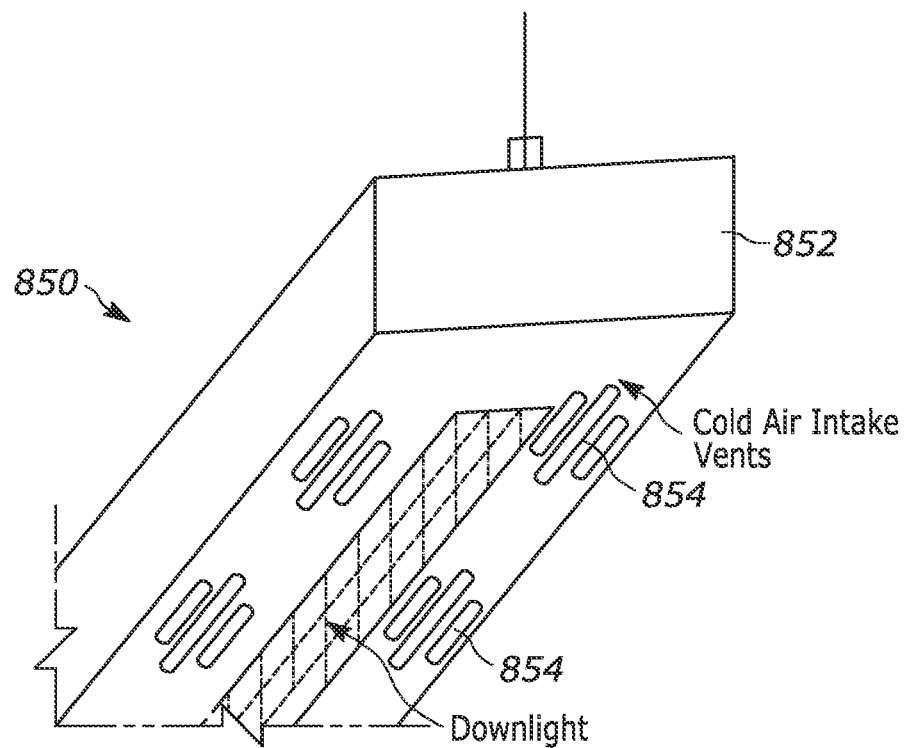
FIG. 25 is a perspective bottom view of an exemplary luminaire incorporating air intake vents and a UV light emitter.
Figure 26:
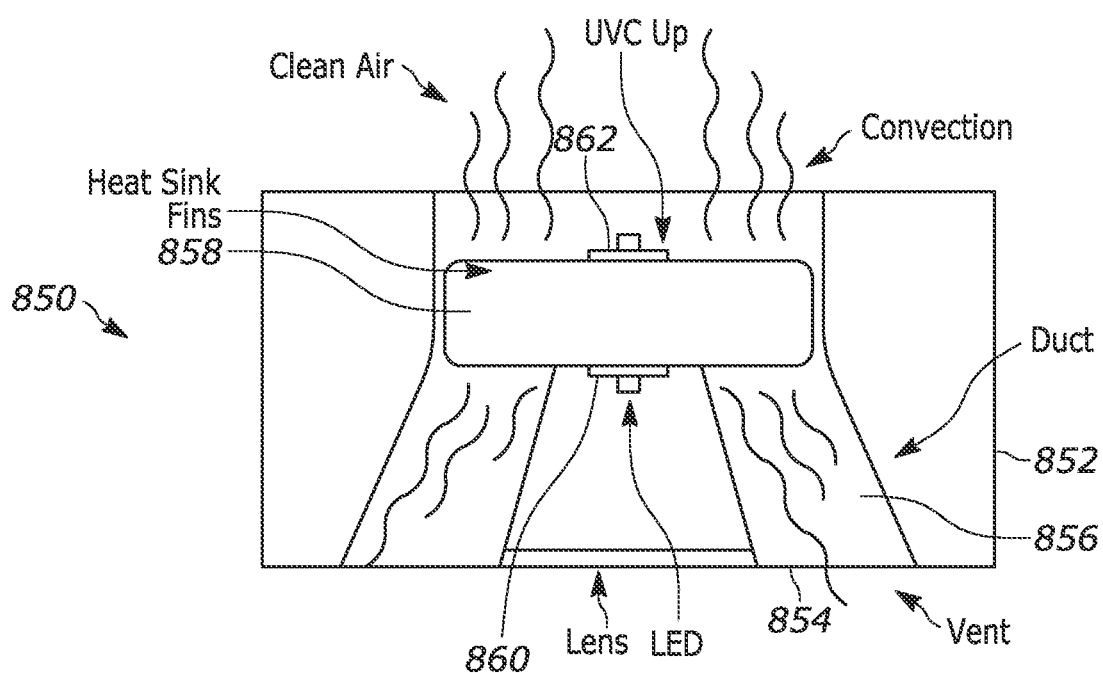
FIG. 26 is a sectional view of the luminaire of FIG. 25.

Certain aspects can utilize natural convection to draw air through a light fixture for disinfection. FIGS. 25 and 26 show an exemplary embodiment of a light fixture 850 illustrated as a linear pendant fixture. The light fixture 850 includes a housing 852 having a bottom wall, top wall, and one or more side walls. A plurality of vents 854 are formed in the bottom wall and top wall to define airflow channels 856 that provide fluid communication through the housing 852.

As best shown in FIG. 26, a heat sink 858 can be positioned in the housing. A first light emitter 860 can be connected to the bottom of the heat sink 858 and a second light emitter 862 can be connected to the top of the heat sink 858. The first light emitter 860 is configured to emit a first type of light, such as visible light in a first direction. The second light emitter 862 is configured to emit a second type of light, such as UV light (e.g., UV-C light) in a second direction. During operation, air flows through the lower vents 854 into the housing 852 and is directed around or through the heat sink 858. The air is exposed to light emitted from the second light emitter 862 which decontaminates the air. The air exits the housing 852 as clean air.

According to certain aspects, multiple UV light sources can be provided and activated independently to increase the life of a light fixture or minimize service time of the fixture. Certain UV bulbs can have a shorter lifespan than other light emitters. To prevent numerous service trips, a light fixture can include multiple UV bulbs that are used independently to extend the life of the fixture. For example, three UV bulbs can be provided in a fixture where the use of only one UV bulb is sufficient. Each of the UV bulbs can be actuated independently, so that the life of the UV aspects of a light fixture are tripled. In some aspects, the bulbs can be activated intermittently on a set schedule, for example the use of one a day or one every hour. In some aspects, the bulbs are actuate sequentially where a first bulb can be used until it burns out, and then the second bulb activated and so on. Different sensors (e.g., light sensors, currents sensors, etc.) can be used to detect bulb burn-out.

Certain embodiments can also incorporate the use of multiple light fixtures positioned in an area (e.g., a room) to balance the disinfectant load of the room. The multiple light fixtures can be used intermittently or sequentially to extend the effective life of an area's system as a whole. Status indicators and communication devices (e.g., NFC, BLUETOOTH, Wi-Fi) can be provided with the light fixtures to provide operating information to users and a remote location.

Figure 27:
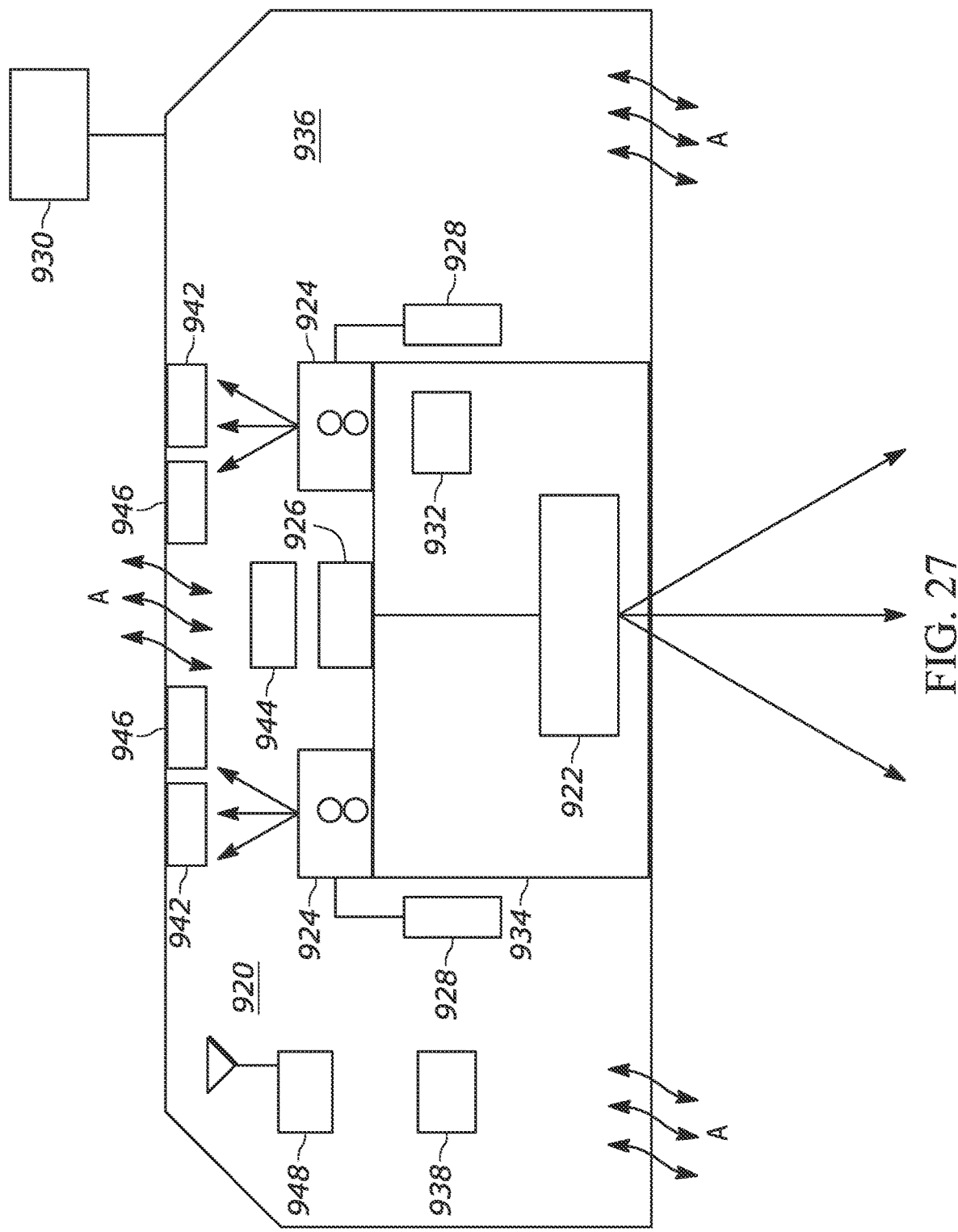
FIG. 27 is a schematic view of a luminaire including an air mover and interior germicidal light emitter.

FIG. 27 illustrates an exemplary schematic of a light fixture 920 having a first light emitter 922 and a second light emitter 924. The first light emitter 922 is positioned in an inner housing 934 and configured to emit a first type of light, such as visible light in a first direction. The second light emitter 924 is positioned in an outer housing 936 and configured to emit a second type of light, such as UV light (e.g., UV-C light) in a second direction. The first direction can be directed to an interior area, such as the floor of a room. The second direction can be directed into the outer housing 936. The outer housing 936 is further configured to permit airflow A through the light fixture 920. This can include vents, channels, conduits, and/or baffles to permit and direct airflow through the light fixture in a controlled manner so that air is decontaminated by the second light emitters 924. While two second light emitters 924 are shown, the number of second light emitters 924 can depend on the configuration of the light fixture 920 and the outer housing 936.

The light fixture 920 includes, among the components described above, an airflow sensor 944, an ozone detector 946, and a UV light sensor 946. Control components 932 monitor the functioning of the components of the light fixture and selectively direct power from the first and second power source 926, 928 to components of the light fixture 920. A throughput of air mover 938 can be controlled by the control components 932, with feedback for such control of air mover 938 provided by airflow sensor 944 to control components 932. An intensity of light output by the first and second light source 922, 924 can also be controlled by the control components 932 based upon feedback from UV light sensor 942 to the control components. Ozone detector 946 can be configured to detect the presence and density of ozone in the air passing through the outer housing before it leaves the light fixture 920. Similarly, UV light sensor 942 can be configured to detect the presence and density of UV light incident to the UV light sensor 942. Control of light fixture 900 components can be provided by the control components 932 based upon such configurations.

The control components 932 use UV light sensor 942 in conjunction with airflow sensor 944 to determine that air passing through the outer housing 936 is being properly bathed in UV light for the purposes of disinfection. In addition, control components 932 use ozone detector 946 to determine that the second light emitter is creating ozone molecules within the air passing through the outer housing 936. The control components 932 are configured to determine whether air passing through the outer housing 936 is being properly decontaminated (e.g. air flow is too rapid for the level of UV to properly decontaminate) and whether an unsafe level of ozone molecules are present in the air leaving the outer housing 936. If an unsafe or inefficient functioning state is detected, the control components 932 control at least one of throughput by air mover 938 or intensity of second light emitter 924 to mitigate or eliminate the detected unsafe or inefficient condition. In addition, in response to detecting an unsafe or inefficient condition, control components 932 use transmitter 948 to communicate a notice indicating the condition to a remote device.

As shown in FIG. 27, redundant, UV emitting bulbs may be used by the second light emitter 924 to ensure that air passing through the outer housing 936 of the light fixture 920 is subjected to an uninterrupted bath of UV light. The control components 932 may be configured detect changes in power drawn by the second light emitter 924 from the second power source 928. In some cases, the control components 932 are configured to recognize a reduction in power drawn by the second light emitter 924 as an indication that a UV-C bulb of the second light emitter 924 is burnt out. In addition, the UV sensors 942 can be monitored by the control components 932 to determine whether a UV-C bulb is properly delivering UV light. If the control components 932 detect via the second power source 928 or the UV sensor 942 that the UV-C bulb of the second light is improperly delivering UV light, the control components 932 deliver power to the redundant UV-C emitting bulb so that the redundant bulb begins producing UV light for the second light emitter 924. Additionally, in response to determining that a UV emitting bulb of the second light emitter 924 may decrease in power usage efficiency or disinfection efficacy, the control components can use the transmitter 948 to communicate a message, to a remote device, indicating that the second light emitter 924 needs to be serviced. Similarly, an indicator light may turn on or off, or indicator speaker may sound to as a notification that the second light emitter 924 is not powered or needs to be serviced.

The second light emitter 924 can also be pulsed to effectively disinfect an area. The control components 932 can be configured to determine a type and quantity of bulbs connected to the second light emitter 924. In response to determining the type and quantity of bulbs connected to the second light emitter 924, the control components 932 control the output of the second power source 928 to deliver the appropriate amount and frequency of power to the second light emitter 924. The duration of each pulse can be adjusted by the needs of the area and the capabilities of the light fixture or other light fixtures associated with the area.

Figure 28:
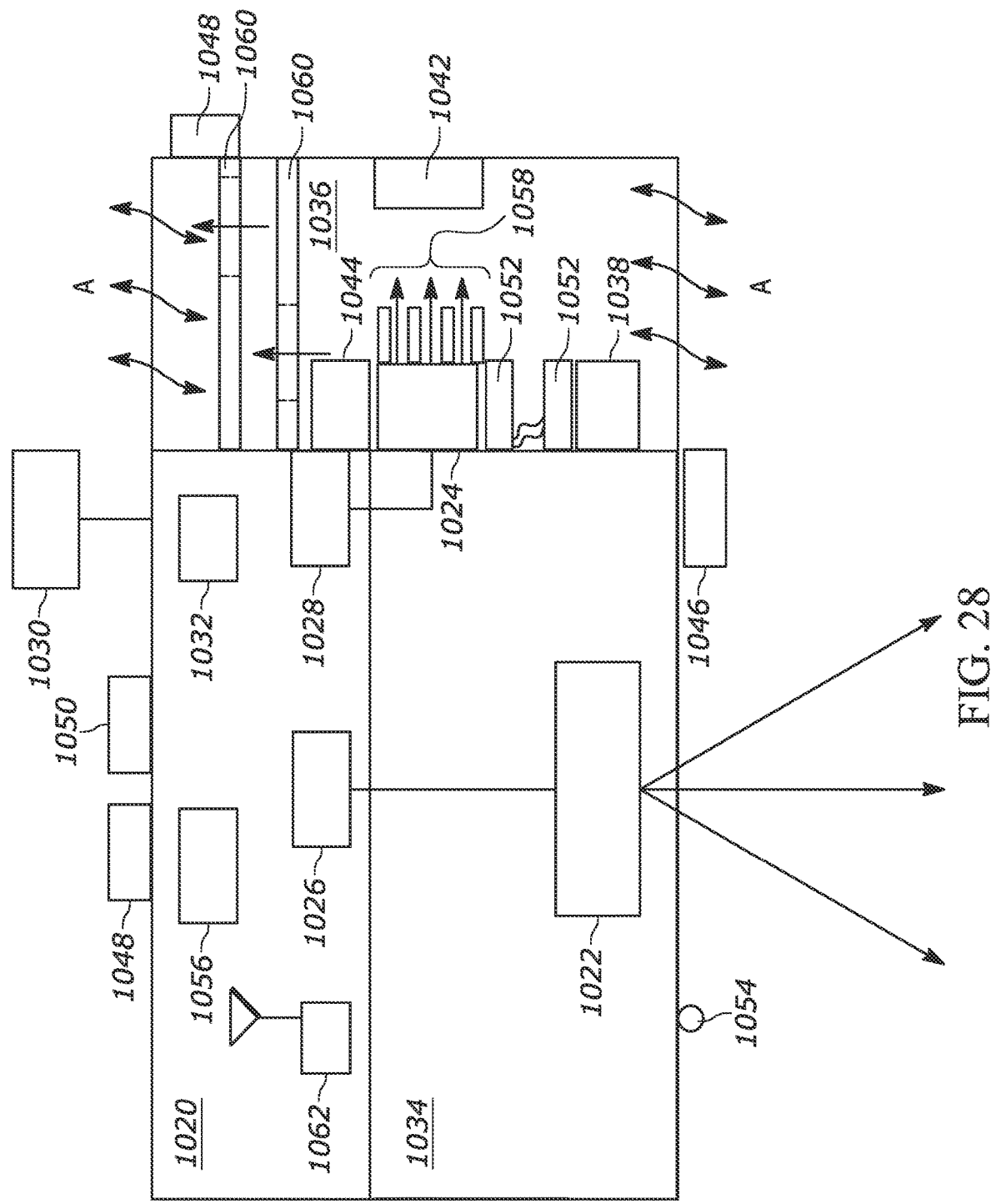
FIG. 28 is a schematic view of a luminaire including an air mover, an interior germicidal light emitter, and interior baffles.

FIG. 28 illustrates a light fixture 1020 including a single airflow chamber in the outer housing 1036. The light fixture 1020 includes, among many of the components described above, an occupancy sensor 1046, fixture movement sensors 1048, speaker 1050, cooling system 1052, indicator light 1054, backup power source 1056, light blade baffles 1058, and UV filter lenses 1060.

In the embodiment shown, the second light emitter 1024 is used in conjunction with light blade baffles 1058 to direct three blades or planes of UV light at UV light sensor 1042. The light blade baffles 1058 may be arranged with more or fewer baffles so that more or fewer blades or planes of UV light are directed at UV light sensor 1042. Similarly, more than one UV light sensor 1042 may be used in conjunction with the light blade baffles 1058 and the second light emitter 1024. The control components 1032 monitor UV light sensor 1042 and airflow sensor 1044 for airflow and UV data. The control components 1032 can correlate the data to determine a disinfections rate with a low margin of error due to the confined nature of the blades of light created by the light blade baffles 1058 affecting the output of UV light by the second light source 1024.

An occupancy sensor 1046 is disposed on underside of the light fixture 1020, granting it visibility of any occupants of a room in which the light fixture 1020 is disposed. The occupancy sensor 1046 may also be disposed on any other portion of the light fixture 1020. The control components 1032 determine via a correlation of data from the UV light sensor 1042 and the airflow sensor 1044 whether radiation generated by the second light source 1024 is flowing out of the light fixture in the airflow created by the air mover 1038. The control components 1032 also determine via the occupancy sensor 1046 whether there is an occupant in the room in which the light fixture 1020 is disposed. In some embodiments, the occupancy sensor 1046 itself includes a UV light sensor 1042 and can be used to determine whether UV light has leaked from the fixture into an occupied room. Based upon any of the above-mentioned determinations, the control components 1032 can be configured to illuminate indicator light 1054 to warn an occupant of the danger of irradiation from the disinfecting action of the light fixture. In addition, the control components 1032 can be configured to deliver an audible warning to occupants via speaker 1050.

The light fixture is 1020 may commissioned in conjunction with the feedback and warning systems described herein to avoid risk of irradiation to humans or the exceeding of a customer chosen UV-light dosage level. In addition, the light fixture 1020 includes fixture movement sensors 1048 that can be configured by a commissioning engineer or technician. The fixture movement sensors may be Doppler effect sensors, distance sensors, accelerometers, gyroscopes, or any other sensor that might evidence movement of the light fixture 1020 to the control components 1032. The commissioning engineer or technician can install the light fixture 1020 and configure the fixture movement sensors 1048 to detect a movement of the fixture. The control components 1032 may monitor the fixture movement sensors 1048, and if a movement of the light fixture is sensed, the control components 1032 light the indicator light 1054 or transmit a notice via transceiver 1062. During initial commissioning, UV sensor cards and ozone test strips can be used to detect hazardous conditions during installation as well, for additional sensing coverage, and if necessary, to calibrate the customer-chosen UV light dosage level.

Disinfection by use of the light fixture 1020 may be scheduled via a connected service and transmitted to the light fixture 1020 and received at transceiver 1062. Control components 1032, being in communication with the transceiver 1062, then establish a scheduled disinfection in onboard memory (not shown) for execution by the light fixture at the established time. In some embodiments, the scheduled disinfection is not established in onboard memory but is transmitted by a cloud service or some other remote computing service at the time of the scheduled disinfection. In such embodiments, the light fixture 1020 immediately executes the scheduled disinfection in response to receiving the scheduled disinfection at the transceiver 1062.

An active cooling system 1052 is used in the light fixture 1020 to ensure that the second light emitter 1024 is properly cooled and is thereby enabled to function at max capacity. In the embodiment shown, the active cooling system 1052 is a liquid cooling system wherein a conductive liquid is used to draw heat away from a heat sink attached to the second light emitter 1024. The heated, conductive liquid is then piped to a radiator where it can be cooled by the airflow generated by the air mover 1038.

UV filter lenses 1060 are disposed in the outer housing 1036. The UV filter lenses 1060 are arranged to allow air to pass through or around them while disallowing any UV light from the second light source 1024 to pass through them. The UV filter lenses 1060 may be staggered or include pass-through apertures (as shows) to accommodate airflow.

To ensure proper airflow and disinfection of air flowing through the outer housing 1036, control components 1032 may periodically generate a reminder to clean the components of the light fixture 1020. This reminder can be communicated by the control components 1032 via the indicator light 1054, the speaker, 1050, or in a message transmitted via the transceiver 1062. Additionally, if airflow sensor 1044 detects low airflow, yet occupancy sensor 1046 detects a lack of occupancy in the area in which the light fixture 1020 is disposed, control components 1032 cause the air mover 1038 to increase airflow to safely optimize the disinfection rate and throughput of the light fixture 1032 in the absence of occupants.

As described above, constant output of UV light results in reliable disinfection of air flowing through the outer housing 1036. In concert with control components 1032, backup power source 1056 can be configured to deliver power to any component of the light fixture 1020 when a loss or reduction in the primary power source 1030 is detected by control components 1032.

Figure 29:
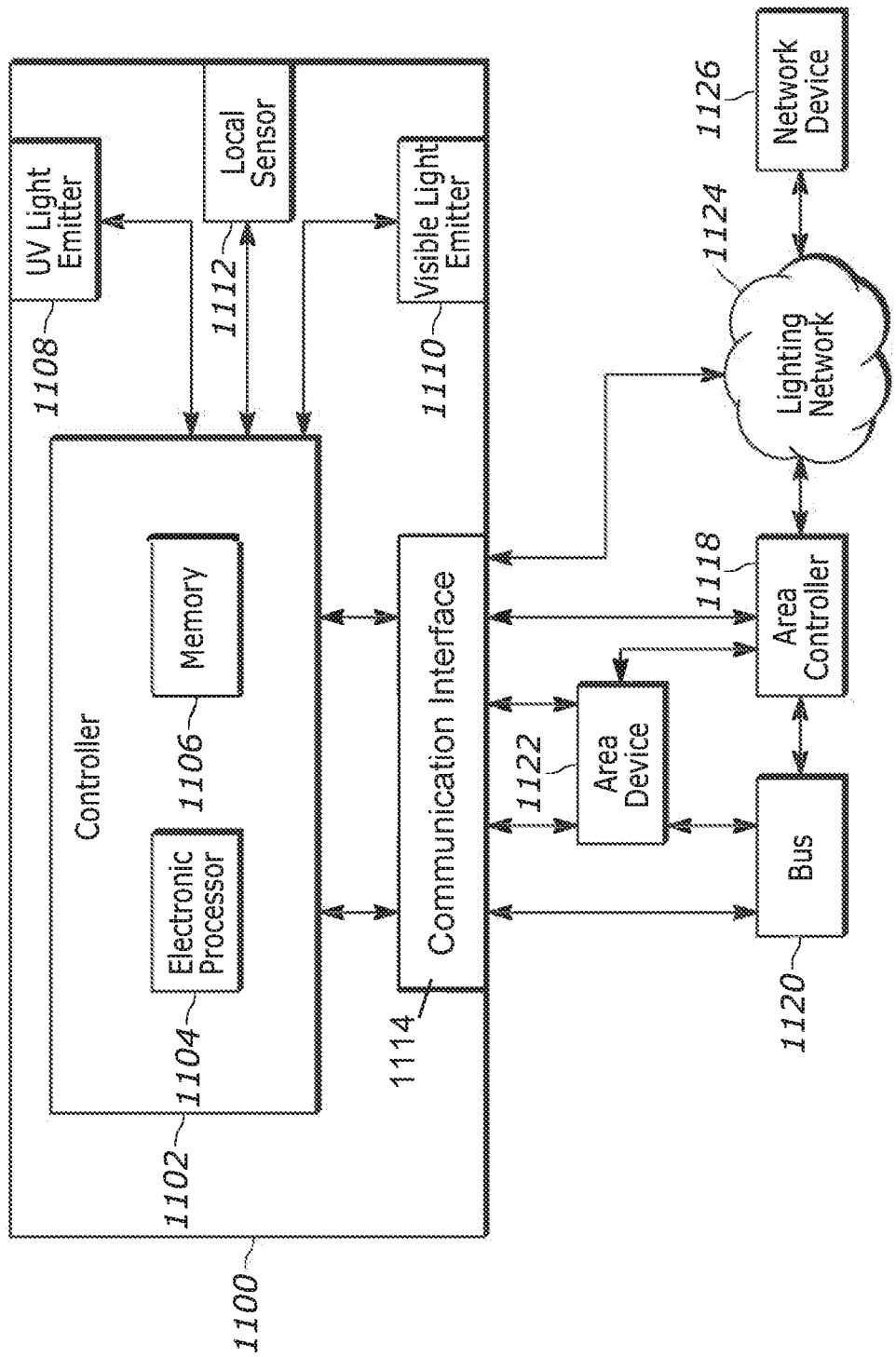
FIG. 29 is a schematic for an exemplary germicidal luminaire connected to a lighting network.

FIG. 29 illustrates a hardware and network configuration for a luminaire 1100 configured to perform ultra-violet disinfection of air. The luminaire 1100 includes a controller 1102 comprising an electronic processor 1104 and a memory 1106. The controller 1102 is configured to control the on/off state, the intensity of operation, and duration of operation of the ultra-violet light emitter 1108, and the visible light emitter 1110 using electronic processor 1104. The luminaire 1100 further comprises local sensors 1112 and a communication interface 1114, and can be configured to perform such control actions in response to an algorithm executed by the controller 1102 (e.g. a scheduled irradiation scheme), or in response to a signal from the local sensors 1112, an area device 1122, the area controller 1118, or the network device 1126 via the communication interface 1114. The communication interface 1114 can include a transceiver that is configured for wireless and wired communication. Wireless communication can include RF, BLUETOOTH, WiFi, NFC, or other wireless communication protocols. Wired communication can include, for example, ethernet communication.

The memory 1106 may store information regarding the intensity and duration of UV light required to be emitted by UV light emitter 1108 to accomplish effective disinfection of a volume of air carrying different types of bacteria or viruses. The electronic processor 1104 is configured to retrieve instructions and data from the memory 205 and execute, among other things, instructions to perform the methods described herein. For example, the memory 1106 may contain tables that correlate the size of a premise to average occupancy of the premise. Such a table may list an appropriate scheduled irradiation scheme for the correlation, and the controller 1102 may be configured to access this table in memory based on data received from local sensors 1112.

The local sensors 1112 may include an occupancy sensor, and environment sensor (e.g. heat, humidity, smoke), or a photosensor. Further, the local sensors 1112 may include a passive infrared (PIR) sensor, an ultrasonic sensor, a dual-tech sensor (that is, a combined infrared/ultrasonic sensor), a microwave sensor, image sensor (e.g., camera sensor) or any other type of sensor. In some cases, the local sensors 1112 capture images (for example, video, still images, or thermal images) of a premise. Additionally, the local sensors 1112 may combine two or more technologies. For example, a microwave sensor may be combined with a thermal imaging sensor to detect people who are moving or being still (for example, a human sleeping in a hospital bed). As will be described in further detail below, the local sensors 1112 may be used in a control scheme wherein controller 1102 controls the operation of UV light emitter 1108 or visible light emitter 1110.

In some embodiments, the communication interface 1114 is configured to transmit data from the luminaire 1100 to an area controller 1118 over an electronic bus 1120. Additionally, the communication interface 1114 is configured to transmit data to the area controller 1118 according to a wireless protocol. The area controller 1118 can receive data transmitted to it by the communication interface 114 and the electronic bus 1120, and is also configured to communicate with at least one area device 1122. Accordingly, the area controller 1118 is also configured to relay data between the electronic bus 1120, the area device 1122, and the luminaire 1100. In some embodiments, the area device 1122 is another luminaire, another sensor, an intermediate device (e.g. an intermediary radio module, a room controller, a switch), etc. connected to the electronic bus 1120.

In some embodiments, the area controller 1118 is also configured to connect the luminaire 1100 and the area device to a lighting network 1124. The lighting network 1124 may comprise an intelligent control and organization scheme for a hierarchy of connected devices including the luminaire 1100, the area controller 1118, the area device 1122, and a network device 1126. The lighting network may expand in size or contract in size as additional devices are each added as a network device 1126 (from the perspective of the luminaire 1100), or connected to the electronic bus 1120, or connected to the area controller 1118 as an area device 1122. The lighting network 1124 may be a wired or wireless network. All or parts of the lighting network 1124 may be implemented using various existing networks, for example, a cellular network, the Internet, a Bluetooth™ network, a wired local area network (for example, Ethernet), a wireless local area network (for example, Wi-Fi), a wireless accessory Personal Area Network (PAN), and a public switched telephone network (PSTN). The lighting network 1124 may also include future-developed networks. As illustrated in FIG. 29, the controller 1102 and a network device 1126 may communicate with each other over the lighting network 1124 using suitable wireless or wired communications protocols. Additionally, local sensors 1112 may communicate with the area device 1122 via communication interface 1114, the area controller 1118, or the network device 1126 over the electronic bus 1120 or the lighting network 1124 using suitable wireless or wired communications protocols. In some embodiments, communications with other components of the system (for example, the area device 1122 and the network device 1126) or other external devices (not shown) occurs over the lighting network 1124.

The network device 1126 may be configured to communicate data over and receive data from the lighting network. For example, the network device 1126 may be a mobile device or personal computer connected to the lighting network 1124 and configured to communicate lighting commands to the area controller 1118 or local controller 1102 via the lighting network 1124. In certain aspects, the area controller 1118 interprets received lighting command and communicates it to the area device 1122 and the luminaire 1100. As another example, the network device 1126 may be another luminaire connected to the lighting network 1124, and may receive lighting commands via the lighting network 1124. As an additional example, the network device 1126 may be another area controller configured to send and receive lighting commands and data over the lighting network 1124, and to distribute those commands to another area device. As yet another example, the network device 1126 may be a sensor configured to collect data regarding the size, air volume of, or occupancy of a premise (for example, a remote premise) or any other type of data, and communicate the data to the luminaire 1100, area controller 1118, or area device 1122 over the lighting network 1124.

The lighting network 1124, the area controller 1118, the area device 1122, and the other components of the system can be configured to perform a timed UV disinfection of a premise using UV light emitter 1108. The timed disinfection may be based upon the premise size, an estimated volume of air to be disinfected, the number connected devices including UV light emitters cooperating in the timed disinfection, or occupancy of the premise. These timed disinfections can be controlled independently for different areas of the premise via the area controller 1118 or local controller 1102 and the lighting network 1124, and may be configured to occur only after occupancy sensors in the area and in communication with the area controller 1118 or lighting network 1124 detect that the area is unoccupied.

In some embodiments, local controller 1102 is configured to execute a scheduled irradiation scheme performed by causing the UV light emitter 1108 to emit UVC light at a pre-determined intensity for a pre-determined duration. The scheduled irradiation scheme generally includes a periodic, timed irradiation performed according to irradiation tolerances determined based on room size, air volume to be disinfected, number of fixtures, or occupancy. For example, the controller 1102 may detect, via the local sensors 1112, a percentage occupancy in the premise in which the luminaire 1100 is positioned. The controller 1102 may access a table in memory 1106 that correlates zone or room size to average occupancy and lists an appropriate irradiation scheme for the correlation. The controller 1102 may then schedule the timing for execution of the irradiation scheme to produce a scheduled irradiation scheme. The controller 1102 may thereafter execute the appropriate scheduled irradiation scheme.

In a some embodiments, the schedule of the timing, duration, and intensity of irradiation by each UV light emitter 1108 is produced by the controller 1102 based on data received by the controller via the lighting network 1124 to area controller 1118 and to bus 1120 (for example, a size of a premise may be communicated to the controller 1102 by a mobile device or cloud computing service communicating with controller 1102 using a Bluetooth of Wifi communication protocol via communication interface 1114). The controller 1102 may then produce or retrieve a schedule irradiation scheme based upon the received data (for example, by accessing a table in memory 1106 based on the data). Additionally the data relevant to the production of the scheduled irradiation scheme by the controller 1102, may be communicated directly to the area controller 1118, to the area device 1122, or the network device 1126 wirelessly by a mobile device, for example, by Bluetooth or Wi-Fi protocol, and those components may then take acting in response to receiving the data (for example, by producing a scheduled irradiation scheme, or by causing a controller of another luminaire to produce a scheduled irradiation scheme).

In a some embodiments, the schedule of the timing, duration, and intensity of irradiation by each UV light emitter 1108 is produced by an external source—such as a mobile software application or cloud computing service—and communicated via the lighting network 1124 to area controller 1118 and to bus 1120. The scheduled irradiation scheme is then communicated to the network device 1126, the area device 1122, or to the luminaire 1100 for execution. Additionally, the scheduled irradiation scheme may be communicated directly to the area controller 1118, to the area device 1122, or the network device 1126 wirelessly by a mobile device, for example, by Bluetooth or Wi-Fi protocol. Further, the scheduled irradiation scheme may be pre-loaded into the memory 1106 of the luminaire 1100 during assembly of the luminaire 1100.

In some embodiments, the luminaire 1100 can act as a standalone device that determines the scheduled irradiation itself, or receives the scheduled irradiation via the area controller 1118, the bus 1120, or the lighting network 1124, and stores the scheduled irradiation in memory 1106 for execution according to the schedule indicated by the scheduled irradiation. For example, controller 1102 may determine the size of a room and the occupancy of the room using local sensors 1112 or based on information taken or received from the area device 1122, the area controller 1118, the bus 1120, the lighting network 1124, or the network device 1126. Controller 1102 may determine that the room is only occupied between 9:00 a.m. and 5:00 p.m., and produce a scheduled irradiation scheme wherein the room is periodically irradiated by UV light emitter 1108 for a predetermined time and a predetermine intensity between 5:30 p.m. 8:30 a.m. In some cases, the local sensors 1112 include only a single sensor, and room size may be assumed by controller 1102, while occupancy is sensed by local sensors 1112. In other cases, room size is sensed by a single sensor of local sensors 1112, while room size may be assumed by controller 1102.

In some embodiments, the local sensors 1112 are configured to detect human occupancy in a room or in certain locations in a room. For example, the local sensors 1112 may include a plurality of sensors. The local sensors 1112 may include electronic or electromechanical devices (for example, transducers), which detect environmental aspects (e.g., motion, sound, light) of a premise and communicate those aspects as electrical signals to the controller 1102. The local sensors 1112 are positioned and configured to sense the presence of one or more humans in a premise. The controller 1102 receives the electrical signals, captured images, or both, and analyzes them to determine whether the premise is vacant or occupied.

In some cases, the controller 1102 determine an occupancy event based on a signal from one or more local sensors 1112. In such a case, the controller 1102 may determine a scheduled irradiation scheme based on at least one disinfection factor and the presence of the human. The scheduled irradiation scheme is executed by the controller 1102, and controller 1102 drives the UV light emitter 1108 to produce UV light. In one example, when the at least one disinfection factor is a type of target bacteria or virus to be damaged or killed. From this, the controller 1102 determines an intensity, duration, and schedule of operation for the UV light emitter 1108. For example, where a person is present, the controller 1102 may reduce the intensity and increase the duration, to reduce the irradiation rate for the occupied room, while still delivering a sufficient dose of UV light to damage or kill the target bacteria or virus.

In some cases, the controller 1102 determines that human is not present in the premise. In such a case the controller 1102 may determine the first drive signal based on the at least one disinfection factor. With regard a target bacteria or virus, a scheduled irradiation scheme is determined by the controller 1102, as described above, except that the intensity, duration, and schedule of operation for the UV light emitter 1108 is not adjusted by the controller 1102 based on the presence of a person. In some cases, if a human enters or leaves the premise, the controller 1102 may adjust or re-determine the scheduled irradiation scheme dynamically, based upon the local sensors 1112 human entering or leaving the premise.

In some embodiments, the controller 1102 is configured to deactivate the UV light emitter 1108 in response to an occupancy event. For example, the controller can determine that a human is present in the premise or in a specific area of the premise and can deactivate the UV light emitter 1108. The local sensors 1112 can include a sensor configured to detect that a human is in danger of harmful irradiation by light emitted by the UV light emitter 1108. The controller 1102 may be configured to turn off the UV light emitter 1108 in response to the local sensors 1112 detection such danger of harmful irradiation. For example, local sensors 1112 may include a camera and an infrared sensor configured to detect a human is or will be within a dangerous proximity of the UV light emitter 1108 as it outputs UV light. Similarly, the local sensors 1112 may be configured to detect that a human is or will be exposed to a harmful amount or intensity of UV light output by the UV light emitter 1108. In some cases, if the controller 1102 shuts off the UV light emitter 1108 in response to detecting a dangerous condition, the controller 1102 may adjust or re-determine the scheduled irradiation scheme based upon the shut off.

In certain aspects, the luminaire 1100 is configured to emit UV light at angles that are above the housing (e.g., at angles greater than 90 degrees relative to the position of the light emitter in the housing). The sensors can be configured to detect occupancy events at or above the housing of the luminaire 1100 to determine that a person is in danger of being exposed to UV light and deactivate the UV light emitter 1108.

In certain aspects, the controller can perform object detection and object recognition to determine if an occupancy event should trigger deactivation of the UV light emitter 1108. The controller can receive images from a sensor 1112 and determine if those images show an occupancy event created by a human versus an occupancy event created by non-human. For example, if a ball in a gym triggers an occupancy event, the controller 1102 can recognize the object as a ball and not deactivate the UV light emitter 1108. If the controller determines that the occupancy even is created by a human enter the UV treated airspace around the luminaire 1100 the controller will deactivate the UV light emitter 1108. Any computer vision or image processing technique suitable for object recognition or detection can be implemented according to example aspects of the present disclosure. As non-limiting examples, image recognition techniques can include pixel analysis, region-based analysis (e.g., R-CNN or R-FCN type analysis), YOLO, SSD, HOG, machine-learned classifiers, etc.

In some embodiments, luminaire 1100 does not comprise UV light emitter 1108, or does not comprise a visible light emitter 1110. Additionally, UV light emitter 1108 and visible light emitter 1110 may be controlled independently of one another or at separate times. In some embodiments, the hardware and network configuration of the luminaire may not include each of the connections shown between components and may comprise additional connections.

It is contemplated that other disinfection methods may be used by the light fixture 1020 in combination with or in lieu of UV disinfection. These other disinfection methods may include chemical disinfection and disinfection by use of microwaves. It is contemplated that when these additional disinfection methods are used by the light fixture 1020, their potentially harmful effects may be contained by use of baffles, filters, blowers, cages, and so forth disposed internal to or external to the light fixture.

It is also contemplated that any of the components described herein may be designed to be UV resistant by use of UV resistant coatings, shields, or isolation from any UV radiation generated by a UV emitting light in order to protect the structure, appearance, and operational integrity of the component.

Certain aspects can also be directed to methods of field commissioning or provisioning UV light fixture systems for a given area. These methods can include the use of UV sensor cards, UV/ozone test strips or other detectors to establish readings and provide adequate coverage. Airflow in a given area can also be measured to calculate disinfectant rates. Acoustic sensing can also be used to provide measurements for commissioning.

The foregoing detailed description of the certain exemplary embodiments has been provided for the purpose of explaining the general principles and practical application, thereby enabling others skilled in the art to understand the disclosure for various embodiments and with various modifications as are suited to the particular use contemplated. This description is not necessarily intended to be exhaustive or to limit the disclosure to the exemplary embodiments disclosed. Modifications may be made to adapt a particular situation or material to the teachings of the disclosure without departing from the scope thereof. Any of the embodiments and/or elements disclosed herein may be combined with one another to form various additional embodiments not specifically disclosed. Accordingly, additional embodiments are possible and are intended to be encompassed within this specification and the scope of the appended claims. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present application, and are not intended to limit the structure of the exemplary embodiments of the present application to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

What is claimed:

1. A luminaire comprising:
a housing configured to be positioned over an area, the housing including a frame having a first channel for receiving a light emitter and a lower channel for receiving a second light emitter;
a light emitter positioned in the first channel, the light emitter configured to emit ultra-violet light;
a second light emitter positioned in a lower channel, the second light emitter configured to emit visible light to the area;
a wall separating the first channel from the lower channel preventing transmission of ultra-violet light between the first channel and the lower channel; and
a reflector assembly connected to the frame to direct ultra-violet light emitted from the light emitter;
wherein at least a portion of the area is located at 0 degrees relative to the light emitter and a majority of the emitted ultra-violet light is emitted from the housing between 90 degrees and 130 degrees relative to the light emitter in a first direction.

2. The luminaire of claim 1, wherein the reflector assembly includes a shield connected to the first channel and positioned over the light emitter, the shield assisting to direct the emitted ultra-violet light from the housing between 90 degrees and 130 degrees relative to the light emitter in the first direction and in a second direction.

3. The luminaire of claim 1, wherein the housing is configured to connect to the wall, the frame includes an inner edge configured to face the wall and an outer edge opposite the inner edge, and the reflector assembly includes an inner reflector positioned between the inner edge and the light emitter and an outer reflector positioned between the light emitter and the outer edge.

4. The luminaire of claim 3, wherein the inner reflector and the outer reflector are independently removable from the housing.

5. The luminaire of claim 3, wherein the inner reflector extends over the light emitter.

6. The luminaire of claim 1, wherein the reflector assembly includes a plurality of lower baffles, each lower baffle having a first portion extending laterally from the light emitter and a second portion extending at an oblique angle from the first portion and away from the housing.

7. The luminaire of claim 6, wherein the reflector assembly includes an upper baffle that is positioned over the light emitter.

8. The luminaire of claim 1, wherein the housing is configured to permit airflow around the light emitter and an airflow sensor and ozone detector are connected to the housing.

9. The luminaire of claim 1, further comprising a controller and at least one local sensor, wherein the controller includes an electronic processor and a memory, the controller in communication with the light emitter, and configured to control an on/off state and a duration of operation of the light emitter according to a scheduled irradiation scheme and the at least one local sensor, and wherein the controller is further configured to detect, via the at least one local sensor, an occupancy event and deactivate the light emitter based on the occupancy event.

10. The luminaire of claim 1, wherein the housing is configured to be wall mounted.

11. The luminaire of claim 1, wherein the housing is configured to be pendant mounted.

12. The luminaire of claim 1, wherein the ultra-violet light is emitted in the range of between 100-280 nm.

13. The luminaire of claim 1, further comprising a controller configured to independently control the operation of the light emitter and the second light emitter.

14. A luminaire comprising:
a housing configured to be positioned over an area, the housing including a frame having a first channel for receiving a light emitter;
a light emitter positioned in the first channel, the light emitter configured to emit ultra-violet light; and
a reflector assembly connected to the frame to direct ultra-violet light emitted from the light emitter, the reflector assembly including a shield connected to the first channel and positioned over the light emitter;
wherein at least a portion of the area is located at 0 degrees relative to the light emitter and a majority of the emitted ultra-violet light is emitted from the housing between 90 degrees and 130 degrees relative to the light emitter in a first direction and in a second direction.

15. The luminaire of claim 14, wherein the housing is configured to be pendant mounted.

16. The luminaire of claim 14, wherein the ultra-violet light is emitted in the range of between 100-280 nm.

17. The luminaire of claim 14, wherein the frame includes a lower channel and a second light emitter is positioned in the lower channel to emit light to the area.

18. The luminaire of claim 17, further comprising a controller configured to independently control the operation of the light emitter and the second light emitter.

\* \* \* \* \*